(12) United States Patent
Anderson et al.

(10) Patent No.: US 8,956,359 B2
(45) Date of Patent: Feb. 17, 2015

(54) METHOD, IMPLANT AND INSTRUMENTS FOR PERCUTANEOUS EXPANSION OF THE SPINAL CANAL

(71) Applicant: Innovative Surgical Designs, Inc., Bloomington, IN (US)

(72) Inventors: D. Greg Anderson, Moorestown, NJ (US); Barry Turner, Columbus, IN (US); Wayne Beams, Bloomington, IN (US)

(73) Assignee: Innovative Surgical Designs, Inc., Bloomington, IN (US)

( * ) Notice: Subject to any disclaimer, the term of this patent is extended or adjusted under 35 U.S.C. 154(b) by 0 days.

(21) Appl. No.: 13/871,183

(22) Filed: Apr. 26, 2013

(65) Prior Publication Data

US 2013/0317509 A1    Nov. 28, 2013

Related U.S. Application Data

(63) Continuation of application No. 12/624,946, filed on Nov. 24, 2009, now abandoned.

(60) Provisional application No. 61/117,726, filed on Nov. 25, 2008.

(51) Int. Cl.

| A61B 17/14 | (2006.01) |
|---|---|
| A61B 17/16 | (2006.01) |
| A61B 17/70 | (2006.01) |
| A61B 17/86 | (2006.01) |
| A61B 17/80 | (2006.01) |
| A61B 17/22 | (2006.01) |

(52) U.S. Cl.
CPC ............ *A61B 17/1637* (2013.01); *A61B 17/14* (2013.01); *A61B 17/1617* (2013.01); *A61B 17/1671* (2013.01); *A61B 17/7071* (2013.01); *A61B 17/8685* (2013.01); *A61B 17/148* (2013.01); *A61B 17/1631* (2013.01); *A61B 17/8004* (2013.01); *A61B 2017/22038* (2013.01)
USPC ......................................................... 606/82

(58) Field of Classification Search
USPC ............ 606/79, 82, 167, 170, 171, 176–179; 600/564–568, 570
See application file for complete search history.

(56) References Cited

U.S. PATENT DOCUMENTS

| 2,072,346 | A | * | 3/1937 | Smith ............................. 27/24.2 |
| 5,591,170 | A | * | 1/1997 | Spievack et al. ................. 606/82 |
| 5,827,305 | A | * | 10/1998 | Gordon .......................... 606/159 |
| 6,746,451 | B2 | * | 6/2004 | Middleton et al. ............... 606/79 |
| 7,927,332 | B2 | * | 4/2011 | Huebner et al. ................. 606/80 |
| 2008/0033465 | A1 | * | 2/2008 | Schmitz et al. ................ 606/170 |

* cited by examiner

*Primary Examiner* — Pedro Philogene
*Assistant Examiner* — David Comstock
(74) *Attorney, Agent, or Firm* — Blank Rome LLP

(57) ABSTRACT

A bone saw including a flexible, rectangular saw blade having a central longitudinal axis and a cutting edge at a distal tip, and a shaft. The shaft has a central longitudinal axis, and a blade passage within the shaft that houses the saw blade, where the central longitudinal axis of the saw blade, of the shaft, and of the blade passage, are parallel. Further included is a blade opening located through a distal end of the shaft and of the blade passage, the blade opening being perpendicular to the longitudinal axis of the shaft. Also, a curved abutment can exist within the blade passage, aligning the saw blade with the blade opening. Distally translating the saw blade within the blade passage can cause the saw blade to conform to the curved abutment and exit the blade opening with the cutting edge essentially perpendicular to the longitudinal axis of the shaft.

18 Claims, 31 Drawing Sheets

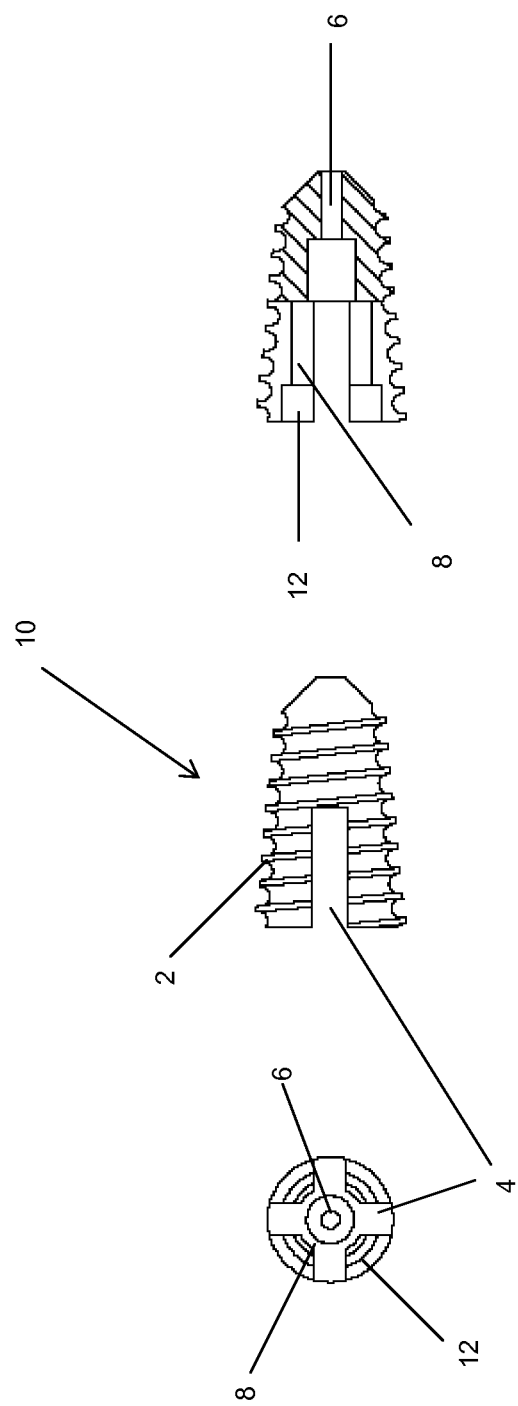

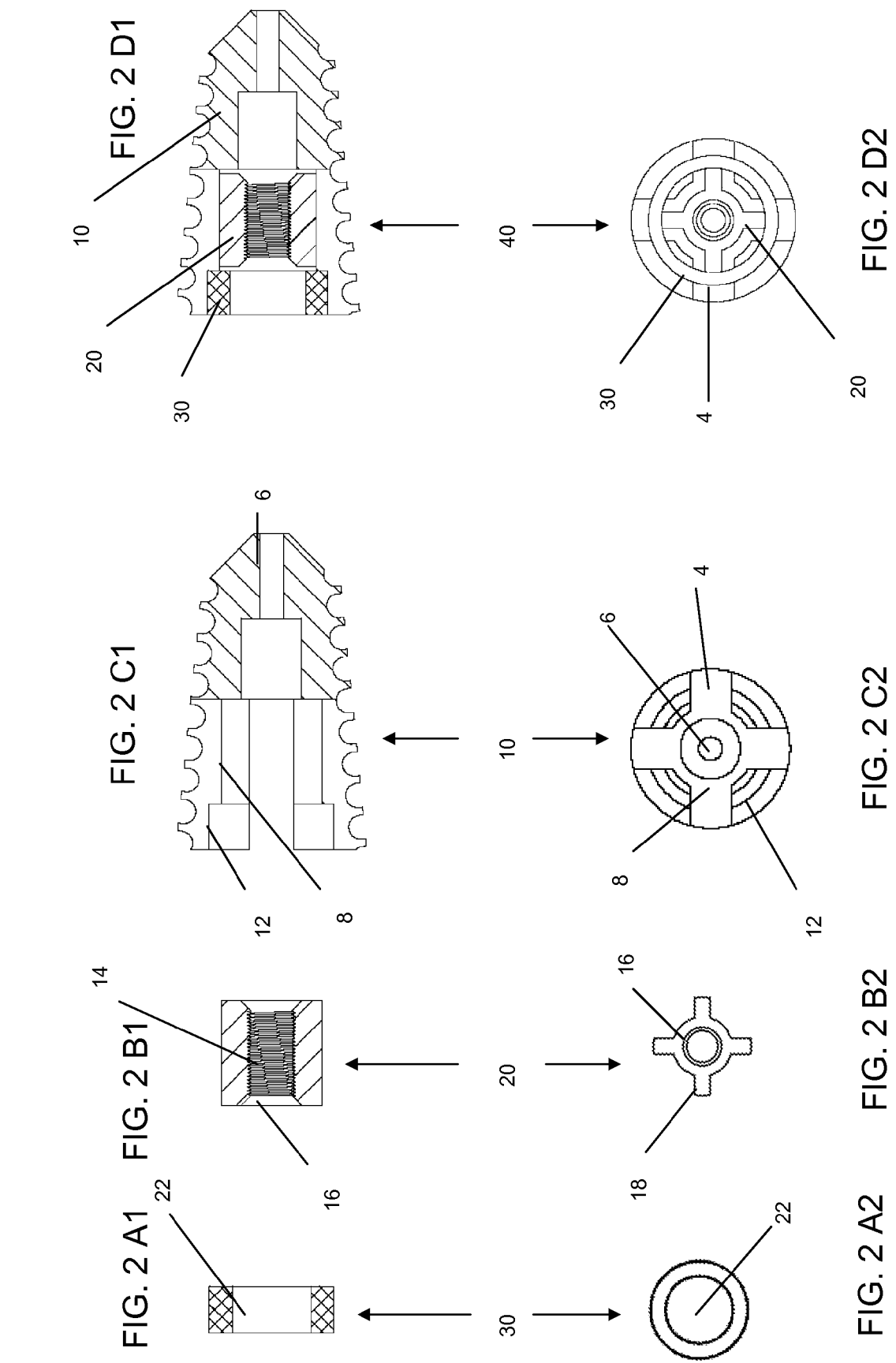

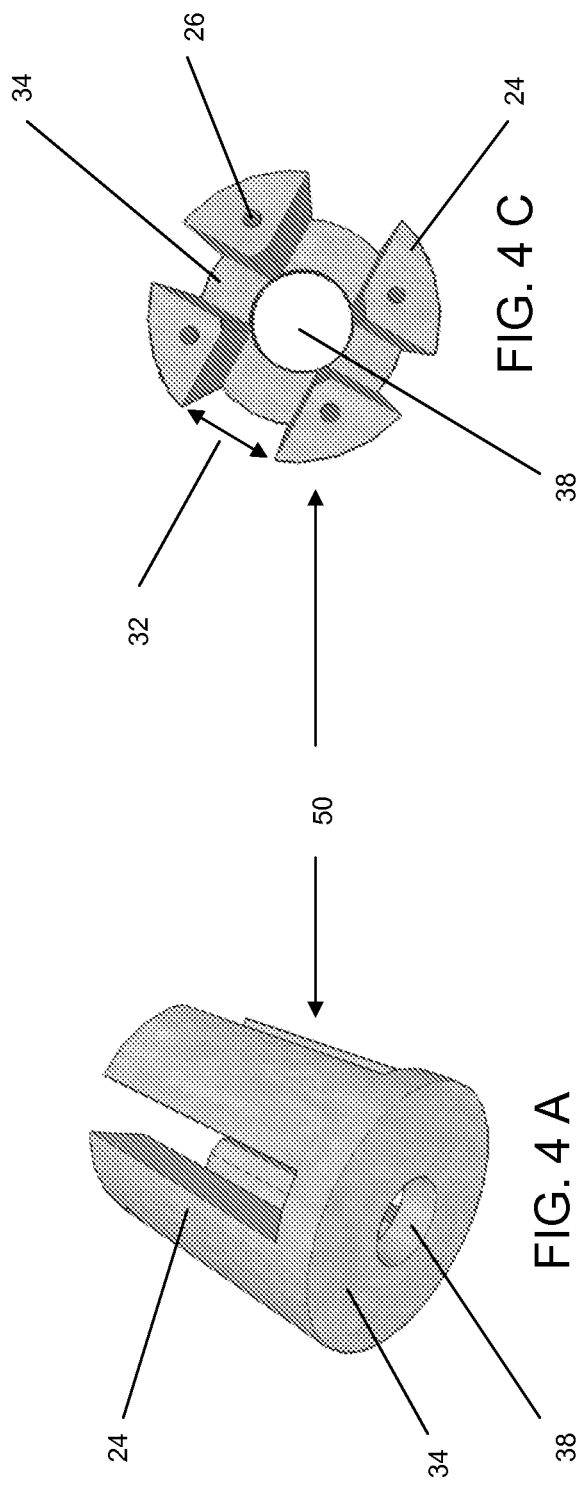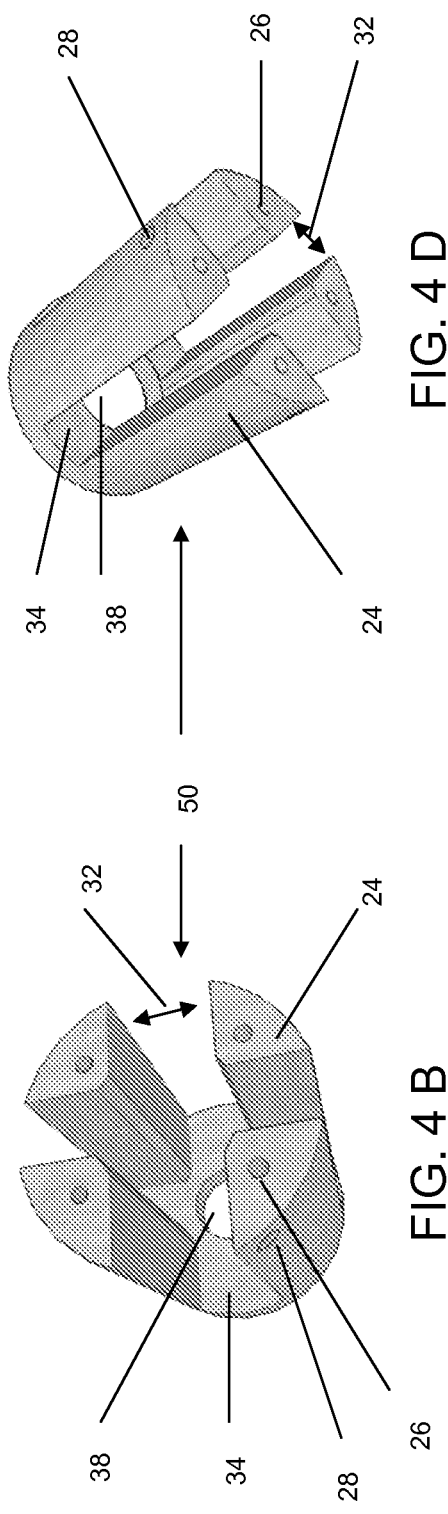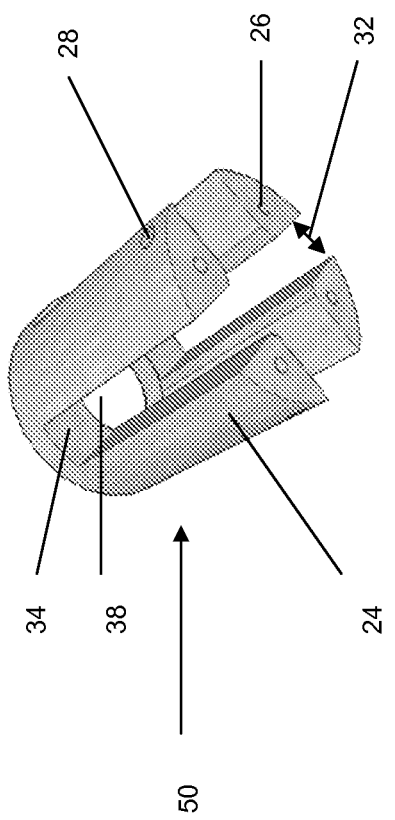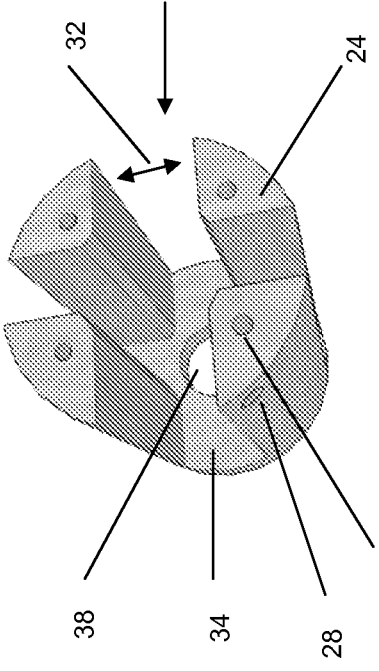

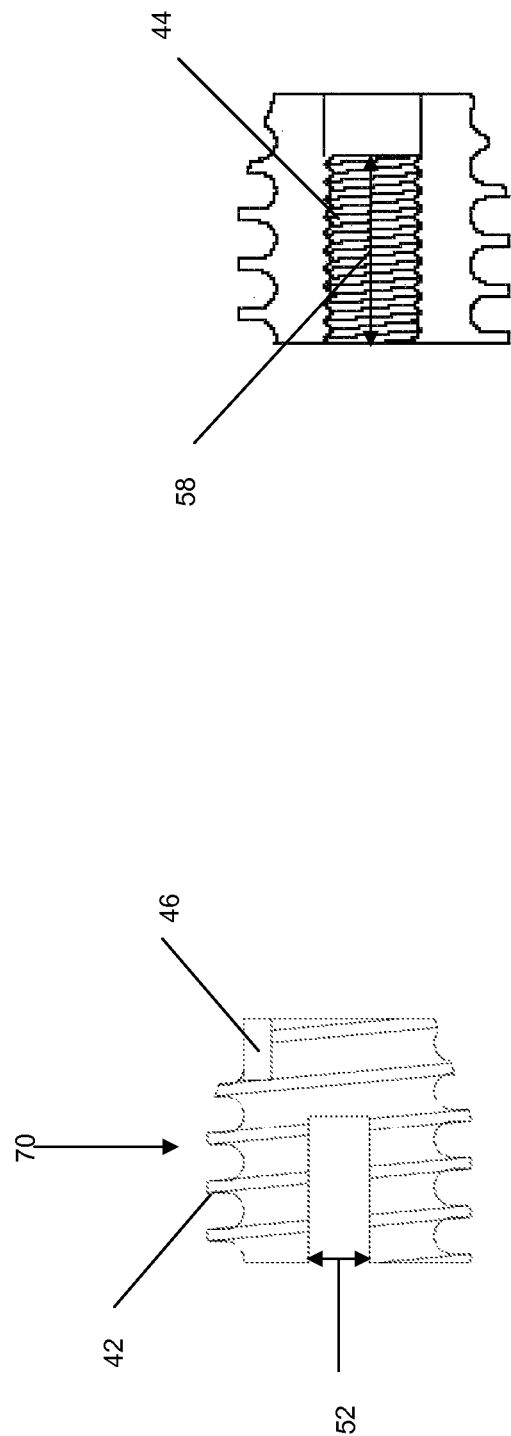

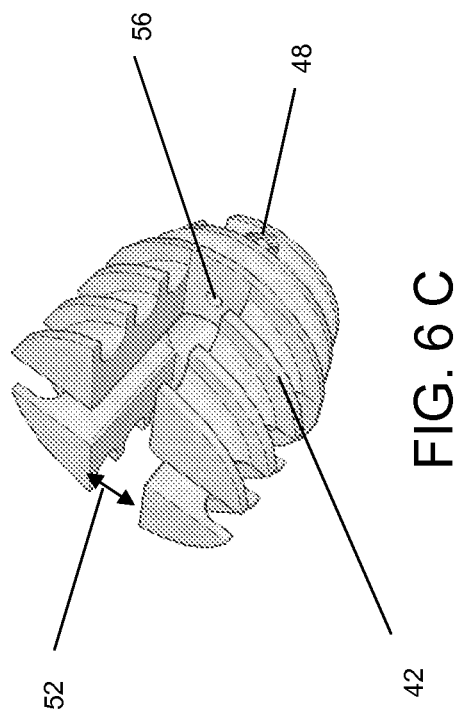
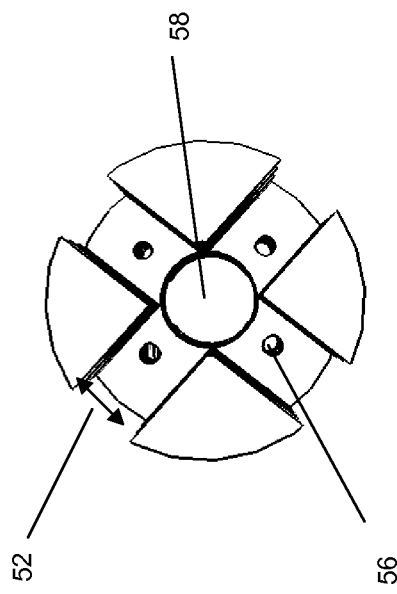
FIG. 6 A
FIG. 6 B
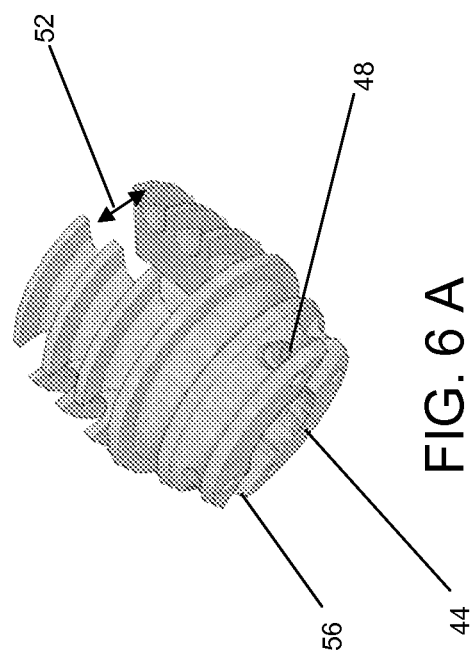
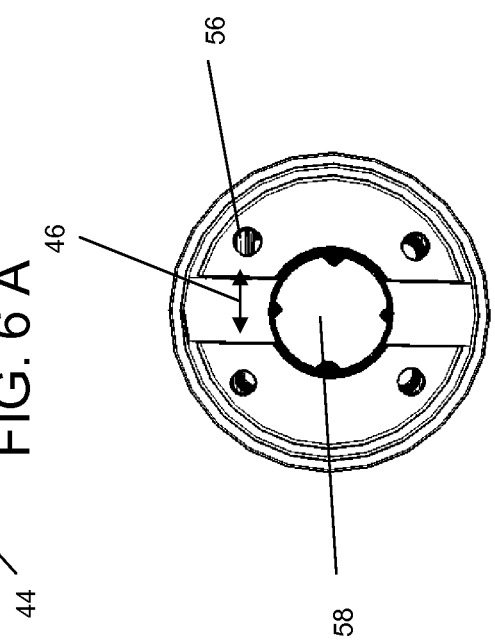
FIG. 6 C
FIG. 6 D

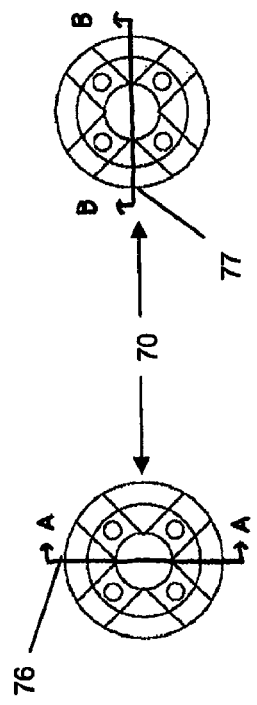
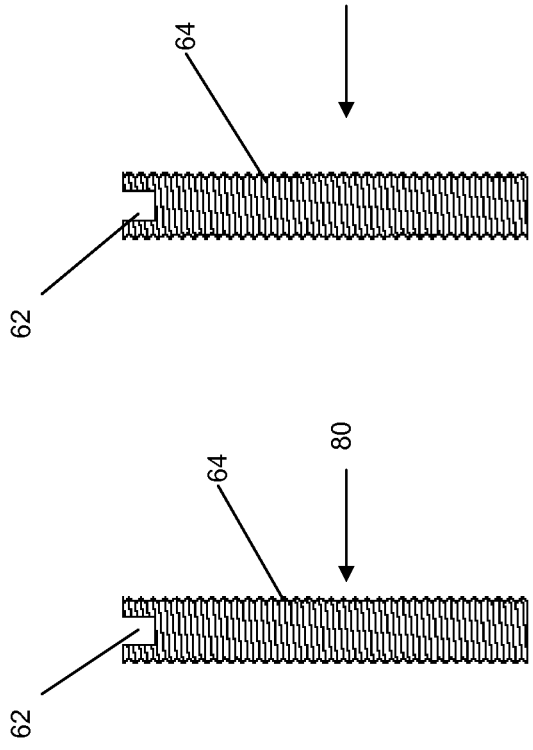
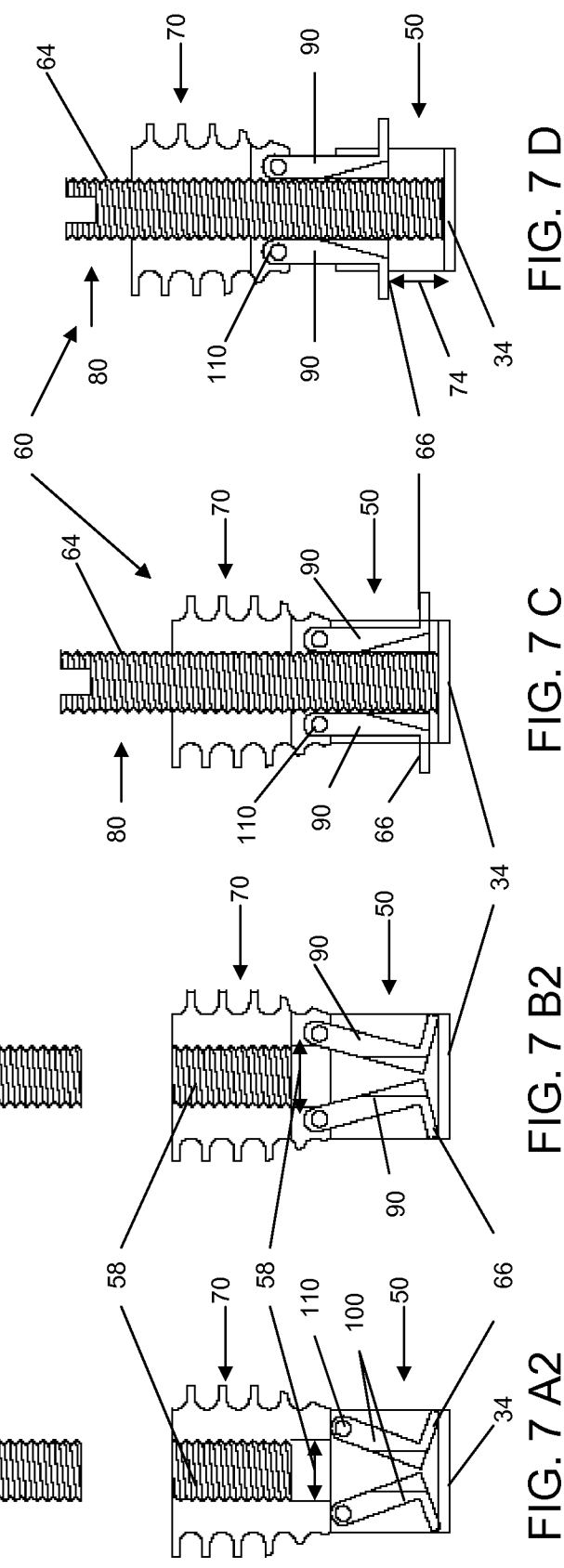

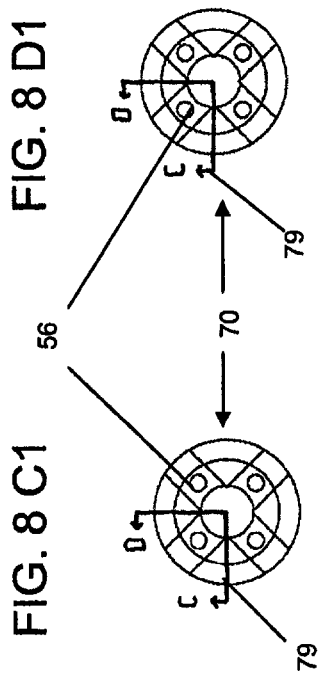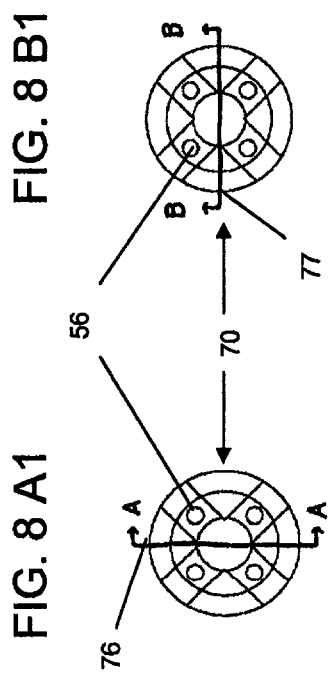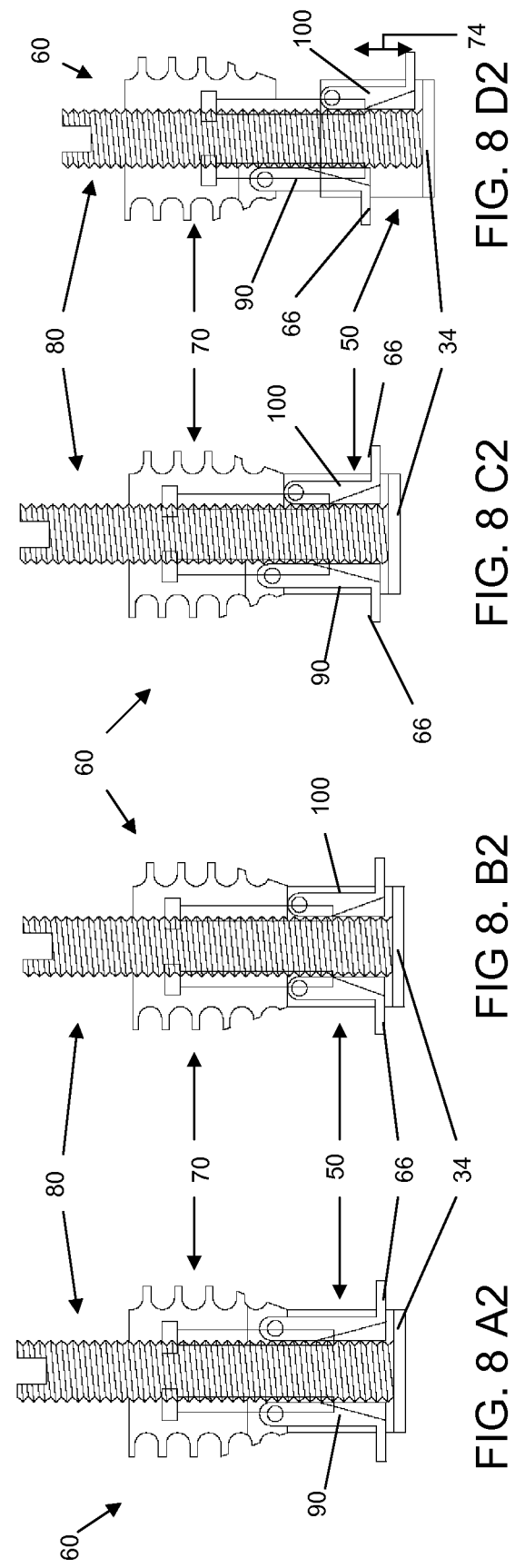

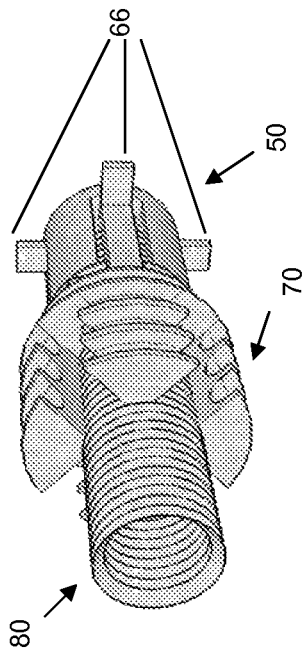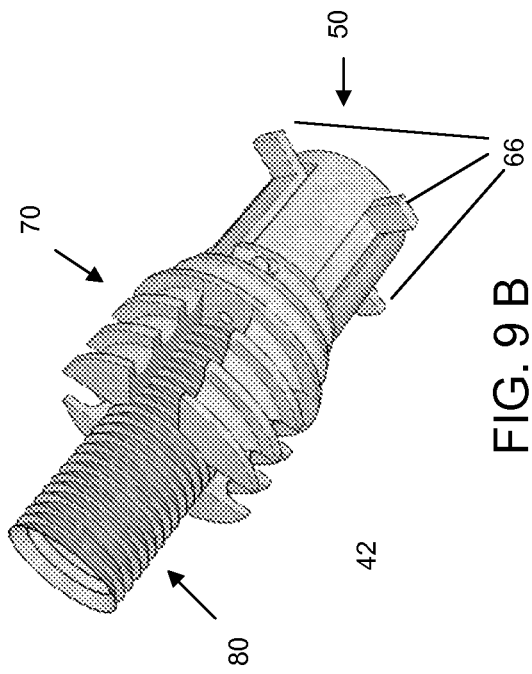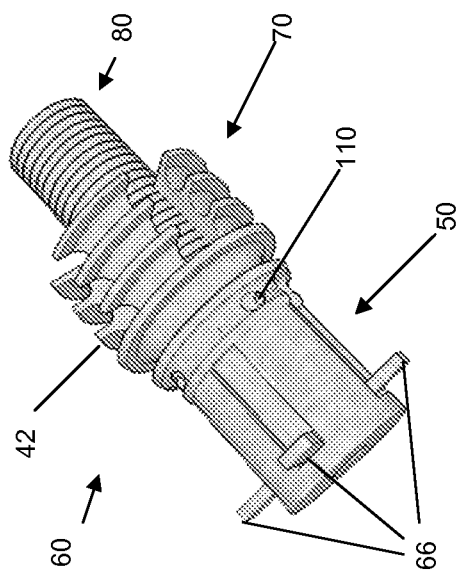

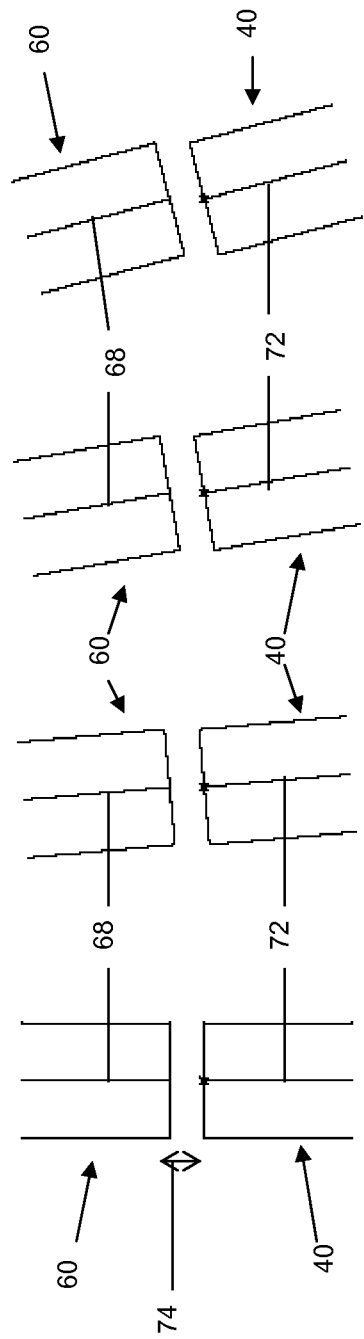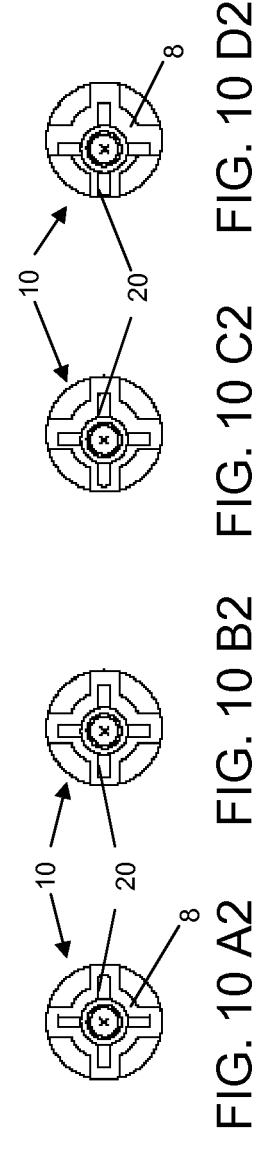

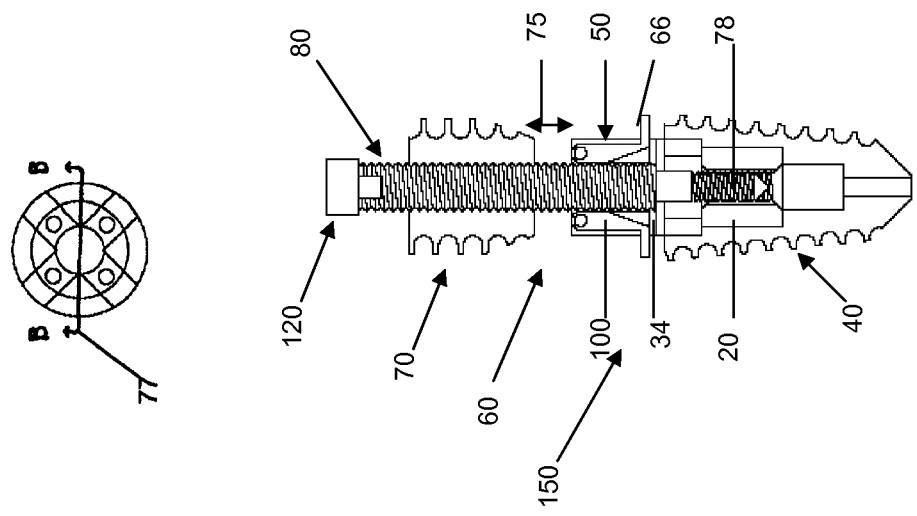
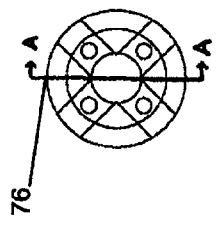
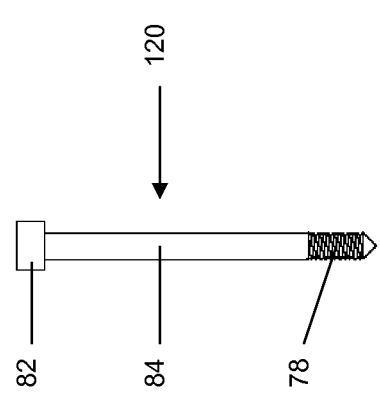
FIG. 11 A
FIG. 11 B
FIG. 11 C

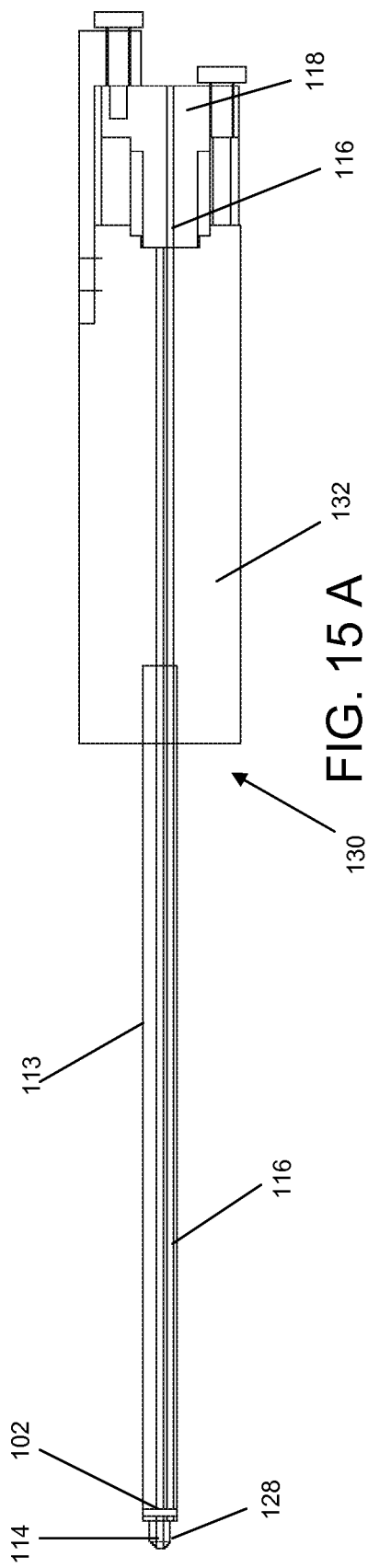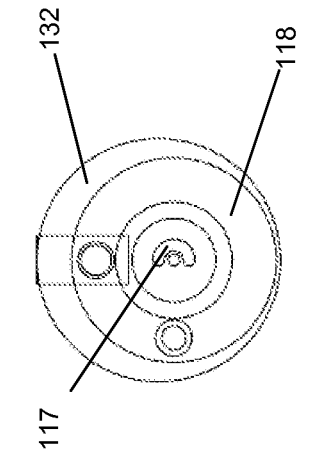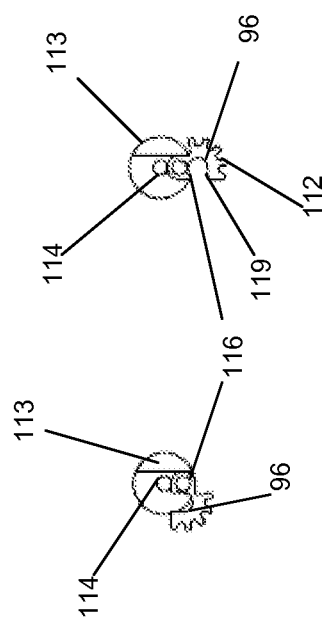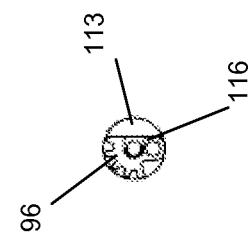
FIG. 15A  FIG. 15B  FIG. 15C  FIG. 15D  FIG. 15E

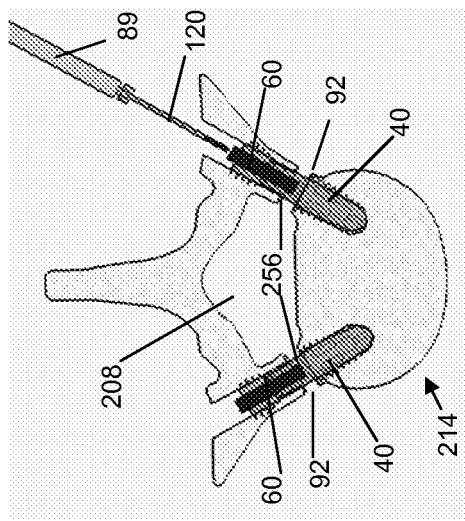
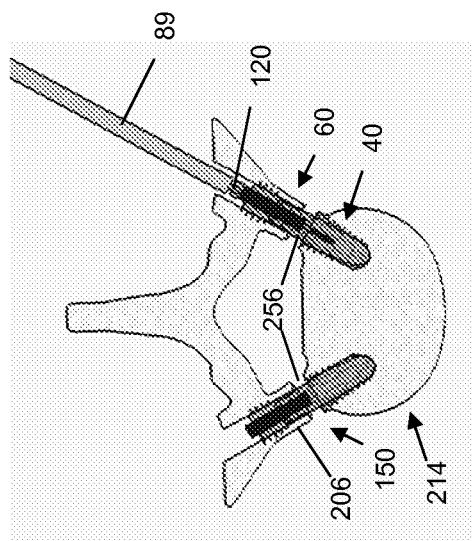
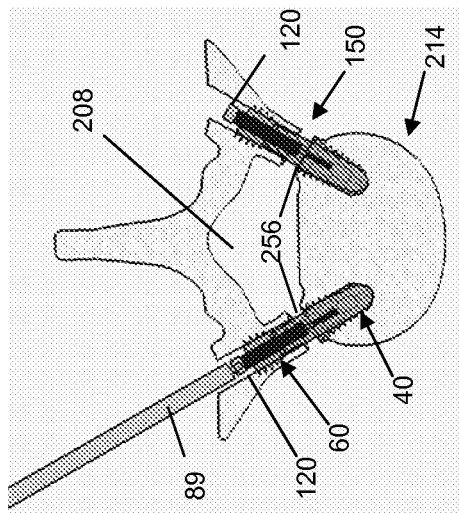
FIG. 30 A  FIG. 30 B  FIG. 30 C

METHOD, IMPLANT AND INSTRUMENTS FOR PERCUTANEOUS EXPANSION OF THE SPINAL CANAL

RELATED APPLICATIONS

This application is a continuation of U.S. Ser. No. 12/624,946, filed Nov. 24, 2009; which application claims benefit of U.S. Provisional Application Ser. No. 61/117,726, filed Nov. 25, 2008, each entitled "Method, Implant & Instruments for Percutaneous Expansion of the Spinal Canal." The above-identified related applications are incorporated herein by reference.

FIELD OF THE INVENTION

The present invention relates generally to spinal surgery, and more particularly to instruments and a device for cutting and lengthening the spinal pedicles to correct spinal canal narrowing or spinal stenosis and to relieve pressure on spinal nerves.

BACKGROUND OF THE INVENTION

Spinal stenosis is a condition or disease causing narrowing of the spinal canal and compression of the spinal nerves. Spinal stenosis affects millions of people world wide and leads to symptoms of back and leg pain, weakness, numbness and trouble walking Spinal stenosis is a particularly common problem among older individuals and can result in severe disability and lack of normal mobility. Spinal stenosis is one of the most common conditions requiring spinal surgery. Surgery for spinal stenosis is required to alleviate compression of the spinal nerves and improve the symptoms of back and leg pain, weakness, numbness and trouble walking.

The traditional surgical operation for spinal stenosis is a called a laminectomy. This procedure involves cutting away the spinal lamina or posterior bony covering of the spinal canal, followed by trimming of the medial portions of the facet joints to expand the room available to the spinal nerves. Some surgeons prefer to use similar procedure called a laminotomy which removes only a portion of the spinal lamina followed by trimming of the facet joints to expand the room available for the spinal nerves.

More recently, implantable medical devices called intraspinous spacers have been used to treat spinal stenosis. These devices are designed to wedge between the spinous processes of two adjacent vertebrae, blocking the vertebral joint from extending or bending backward. Because the spinal canal becomes most narrow in the extended position, intraspinous devices can help a subset of spinal stenosis patients that only experience pain while standing.

Although laminectomy, laminotomy and intraspinous spacer devices may all be successful for patients with spinal stenosis, each of these approaches has significant limitations in a significant proportion of patients with spinal stenosis. For instance, laminectomy generally is a major spinal operation requiring general anesthesia which can lead to complications especially in older patients. Several important disadvantages have been identified with the use of laminectomy to treat spinal stenosis such as damage to back muscles, destabilization of the spine and scarring around the nerve roots. In some cases, destabilization of the spine may cause a serious forward slippage of one vertebra on the adjacent vertebra requiring a major revision surgery called spinal fusion. Also, laminectomy requires a large surgical incision, leading to the risk of major bleeding and the need for general anesthesia. Because most patients with spinal stenosis are elderly, major surgery such as laminectomy may lead to medical complications, making this approach suboptimal for the older, medically fragile patient. In addition, laminectomy may not provide a permanent cure for spinal stenosis, which recur causing the need for further major surgery in the future.

Laminotomy is quite similar to laminectomy but does not require removal of the entire bony lamina. Like laminectomy, laminotomy is normally performed under general anesthesia and involves trimming away portions of the spinal lamina and facet joints to decompress the spinal nerves. Advocates of laminotomy believe that the laminotomy approach may lessen the risks of spinal destabilization and nerve scarring compared to laminectomy. However, laminotomy still requires major open spinal surgery and general anesthesia. It also is more technically difficult to perform compared to laminectomy and may not adequately relieve the pressure on the spinal nerves. In addition, there is a risk that with time, the spinal stenosis may recur, leading to the need for additional surgery.

Recently, intraspinous process spacers, such as the device described by Zucherman, et. al. (U.S. Pat. No. 5,836,948) have been described for the treatment of spinal stenosis. These devices are designed to be wedged between the spinous processes, and block the vertebral joint from assuming an extended position. Because the extended position causes the spinal canal to be smaller, the avoidance of this position may alleviate the symptoms of spinal stenosis in a subset of patients with symptoms only while standing (or bending backward; i.e., extending) that are relieved with sitting (or bending forward; i.e., flexing). This subset of patients generally have less severe narrowing of the spinal canal and may achieve relief of pain by blocking the position of the vertebral joint leading to the worst narrowing of the spinal canal.

Unfortunately, intraspinous devices only provide a slight expansion of the spinal canal compared to laminectomy and laminotomy. Thus, intraspinous spacers are only useful in the subset of spinal stenosis patients with relatively mild stenosis. Also, because the narrowed spinal canal is not significantly enlarged, and because the narrowing of the spinal canal worsens with time, intraspinous process device may only provide temporary relief of the symptoms of spinal stenosis. Thus, many patients treated with laminectomy may ultimately require a laminectomy as their condition worsens. Also, intraspinous process spacers are not able to be used in patients whose spinous processes are weakened by osteoporosis or absent due to a prior laminectomy procedure.

For all these reasons, a better treatment approach to spinal stenosis is needed. In U.S. Pat. No. 6,358,254, issued Mar. 19, 2002, entitled "A Method and Implant for Expanding a Spinal Canal," and in U.S. Pat. No. 7,166,107, issued Jan. 23, 2007, entitled "Percutaneous Technique and Implant for Expanding the Spinal Canal", novel inventions are disclosed whereby the spinal canal can be expanded by cutting and lengthening the spinal pedicles. The present invention describes further, novel instruments, devices, spinal implants and methods pertaining to the art of pedicle lengthening that can be used to expand the spinal canal for the correction of spinal stenosis. The present invention provides significant advantages compared to the prior art methods and devices for treating spinal stenosis.

In U.S. patent application Ser. No. 10/386,357 (US 2003/0212400) to Bloemer et al., a method for expansion of the spinal canal is disclosed. In Bloemer, spinal stenosis is treated by cutting, distracting and holding spinal pedicles with implanted devices. However, the approach of Bloemer has certain limitations and disadvantages that severely limit its usefulness for treating spinal stenosis. First, no cutting method or tools disclosed by Bloemer allow the bone cuts to be performed. The work of the present invention has demonstrated that safe and accurate cutting of the spinal pedicles is highly complex given the dense bone of the spinal pedicles and the close proximity of the bone cuts to the delicate nerve tissue and fluid filled dural sac. In addition, the shape of the spinal pedicles is not regular but rather the bone of the pedicle forms an irregular shape in cross section that resembles an oval. In addition, the bone of the pedicle has thick and thin regions which make the cutting task a substantial challenge for which no instruments or tools have been previously known to the art of spine and bone surgery.

Second, the implants disclosed by Bloomer fail to gain purchase within the pedicle bone cut, but rather rely on bony purchase within the pedicle bore. Research surrounding the present invention has shown that due to the soft or poor quality bone within the upper region of the pedicle, an implant as disclosed by Bloemer would not gain adequate bony purchase to achieve the distraction force necessary to create a gap within the pedicle sufficient in size to expand the spinal canal.

Third, the device of Bloemer does not provide for the geometric offset that tends to occur during pedicle lengthening. Because of the lateral to medial angulation of the pedicles, there is the potential for the pedicle lengthening maneuver of the pedicles to produce a malalignment between the upper (proximal) and lower (distal) portion of the implant. This potential problem was not anticipated by Bloemer, and thus no mechanism to contend with geometric offset was disclosed by Bloemer.

Fourth, the disclosure of Bloemer provides no means to precisely align the pedicle cut with the portion of the implant that performs the pedicle lengthening maneuver. Proper alignment of the implant with the pedicle cut is crucial for the pedicle lengthening device to work correctly and yet no means to achieve this alignment was disclosed.

For all these reasons, Bloemer fails to provide a workable concept to achieve pedicle lengthening for the correction of spinal stenosis. Not surprisingly, the work of Bloemer has not been reduced to practice within the field of spine surgery, nor has research on the technique been disclosed in the public domain. Therefore, additional novel inventions are required to overcome these limitations and provide a functional means for achieving a correction of spinal stenosis through pedicle lengthening.

In view of the foregoing, a new, less invasive method to correct spinal stenosis without the limitations of current methods is needed to address the disabling symptoms suffered by millions of individuals with spinal stenosis. The optimal treatment method must be safe, reproducible, effective in eliminating nerve pressure and minimally invasive so that older patients or those with health problems could be treated without the need for major, risky surgery. The present invention achieves these goals.

SUMMARY OF THE INVENTION

The present invention comprises novel instruments for cutting the spinal pedicles in precise and reproducible location without injury to the surrounding delicate nerve tissue or fluid filled nerve sac. Also disclosed are novel spinal implants and devices capable of aligning the pedicle cut precisely to the spinal implant, performing the distraction of the pedicle cut and fixating the cut in the expanded state to allow bony healing to occur, thus permanently expanding the spinal canal. Further provided are spinal implants capable of gaining bony purchase at the site of the pedicle cuts to provide adequate grip of bony structure to allow pedicle distraction to be achieved.

In addition, a novel mechanism is provided, allowing for connection between the upper (proximal) and lower (distal) portions of the implant, even in the setting of misalignment which may occur during the pedicle lengthening process. Also disclosed is a simple, reproducible means of performing the pedicle lengthening procedure in the human spine through a percutaneous technique to relieve pressure on the spinal nerves.

Embodiments of the present invention will be shown variously to:

maintain the integrity of the spinal canal while expanding the space available for nerve tissue; avoid surgical scarring around the spinal nerves such as would be expected with a laminectomy or laminotomy procedure;

avoid creating of spinal instability while expanding the area available to the nerve tissue;

decompress spinal nerves with a quick, safe and minimally invasive approach;

provide a long term solution to spinal stenosis with minimal risk of recurrent stenosis;

expand the spinal canal using only small, percutaneous skin incisions;

allow the pedicle lengthening procedure to be performed under local anesthesia;

reliably and safely cut the spinal pedicle from within a bore or passage within the pedicle;

provide a means to precisely align the spinal implant with the bone cut so reliable lengthening of the pedicles is achieved;

provide a means to mechanically purchase the stronger cortical bone at the site of the bone cut during pedicle lengthening;

provide a reliable means to ensure that the bone cut is performed in precisely the correct location within the spinal pedicle;

provide a means of lengthening the pedicle a set distance during the lengthening procedure;

provide a means to accommodate a change in the position or alignment between the upper and lower portions of the implant (a proximal and distal portion) during the lengthening procedure;

provide a means of locking the proximal and distal portions of the implant together after the lengthening maneuver;

provide a means to gain mechanical purchase of the bone on both the proximal and distal portions of the osteotomy, to provide resistance to multidirectional biomechanical forces during healing of the bone cut;

provide a means to perform the pedicle lengthening procedure over a guide wire to ensure ease of the operative steps;

provide bone threads on the implant optimized for purchase of the spinal bone;

provide resistance to excessive bone stress during the pedicle lengthening procedure;

provide a means to lengthen the pedicle osteotomy using a controlled, threaded mechanism; and provide a means to secure the pedicle lengthening implant in place to allow for bone healing at the site of the bone cut.

In one aspect of the present invention, a method for correcting spinal stenosis is disclosed whereby the spinal canal is substantially enlarged. First, at least one passage is created, or cannulated, into a vertebra. The passage can be created through the long axis of the spinal pedicles at one or more vertebral levels. Here, an enlarged bone bore can be prepared along the axis of the pedicle on each side of the spine to create a hollow column of bone with intact bony cortical walls.

Next, a distal portion of an implant is placed into the passage. A proper depth of the implant can be visualized with radiographic imaging. Next, a circumferential vertebral cut is performed, using one or more bone saws, from within the passage, through to the spinal canal and through to an outside of the vertebra, using a proximal end of the distal portion of the implant to align the vertebral cut.

After the cut, a proximal portion of the implant is placed into the passage. A distal end of the proximal portion of the implant is positioned against the proximal end of the distal portion of the implant at the vertebral cut. Then, operation of the distal and the proximal portions of the implant relative to one another widens the vertebral cut and expands the spinal canal.

Prior to vertebral cut widening, internal implant components can be manipulated to deploy fins into the bone cut, or into the passage side walls, resulting in good bony purchase of the proximal and distal portion of the vertebral cut. Then, internal implant components can again be used to elongate the distance between the proximal and distal portions of the implant to widen or expand the gap, at the site of the bone cut. Next, an internal connecting means can be used to secure the proximal and distal portions of the implant together to secure the bone cut in the elongated position. Finally, a locking means can be used to secure the implant so that the component are locked into position to allow for healing of the pedicle cuts in the expanded position thus correcting the narrowing of the spinal canal.

In one preferred embodiment, the at least one passage and the vertebral cut extend through a pedicle of the vertebra, and where widening the vertebral cut elongates the pedicle, thereby increasing an area of the spinal canal. The vertebral cut can be located in a lumbar vertebra.

Further, a preliminary step might introduce a guide wire into the vertebra to guide a drilling of the at least one passage into the vertebra. In this preliminary step, a cannulated drill is positioned over the guide wire to drill the at least one passage into the vertebra.

As introduced above, in one preferred embodiment, during operation of the distal and the proximal portions of the implant, at least one flange radially extends outward from the implant and into the vertebral cut, assisting the widening of the vertebral cut and a stabilization of the vertebral cut. Alternatively, or in addition to, at least one flange can radially extend outward from the implant and into the passage to engage side walls of the passage, thereby facilitating stabilization of the implant within the passage.

In another aspect of the present invention, an implant for expanding a spinal canal is provided, and includes a distal portion, a proximal portion including a threaded device and an expanding device, and a screw communicating with the threaded device and the expanding device. Herein, operation of the screw can move the expanding device relative to the threaded device to increase a length of the proximal portion. The increasing length of the proximal portion, bearing against the distal portion, acts to widen a vertebral cut to expand the spinal canal. Moving the expanding device relative to the threaded device might involve a screw, threadably engaging an inner channel of the threaded device, and abutting a base of the expanding device, to translate the expanding device away from the threaded device, upon operation of the screw, to widen the vertebral cut.

The implant can further include a locking bolt configured for insertion through the proximal portion and into the distal portion. Engagement of the locking bolt with the proximal and the distal portions fastens the implant about the vertebral cut. The vertebral cut is then stabilized, allowing vertebral healing with the spinal canal expanded.

In this aspect, the distal portion might further include a floating nut movably housed therein. The movable configuration of the floating nut within the distal portion can assist acceptance of the locking bolt within the distal portion, after insertion through the proximal portion, even if a longitudinal central axis of the proximal and the distal portions becomes translationally malaligned during vertebral widening.

Concerning the radial flange aspect of the invention, the one or more flanges might be movably attached to the threaded device. Here, operation of the screw causes the at least one flange to project radially from the proximal portion, into the vertebral cut, prior to a lengthening of the proximal portion to widen the vertebral cut. Upon radial projection of the at least one flange into the vertebral cut, the one or more threaded device flanges might bear against a proximal side of the vertebral cut during and assisting vertebral widening.

Further, the expanding device might also include one or more flanges configured to project radially from the proximal portion, into the vertebral cut, during operation of the screw. Still further, the at least one expanding device flange, upon radial projection into the vertebral cut, might bear against a distal side of the vertebral cut during and assisting vertebral widening. The flanges can include osteoconductive, osteoinductive or osteogenic material to assist with healing of the vertebral cut.

In another aspect of the invention, an implant for expanding a spinal canal includes a distal portion having inner threads, a proximal portion having inner threads, and a screw. In this aspect, the inner threads of the distal portion are of a substantially different pitch than the inner threads of the proximal portion, creating a dual pitch configuration. The screw is capable of communication with the distal and the proximal portions, and has outer threads at a distal end substantially similar in pitch to the inner threads of the distal portion, and outer threads at a proximal end substantially similar in pitch to the inner threads of the proximal portion. In this aspect, operation of the screw within the distal and the proximal portions translates the proximal portion relative to the distal portion, due to the dual pitch configuration, about a vertebral cut, to widen the vertebral cut and expand the spinal canal.

In one embodiment, the distal portion and the proximal portions each further include external threads to engage an interior of a passage within a vertebra, the outer threads of the distal portion engaging the interior of the passage on one side of the vertebral cut and the outer threads of the proximal portion engaging the interior of the passage on another side of the vertebral cut.

Fins or flanges can be employed in the dual pitch implant as well. In one aspect, the distal portion and/or the proximal portion further comprise at least one flange movably attached thereto, configured to project radially from the distal portion, into an interior of a passage within a vertebra, to facilitate stabilization of the distal portion within the passage during operation of the screw and widening of the vertebral cut. In this aspect, insertion of the screw within the distal portion causes the at least one flange to project radially from the distal and/or the proximal portions into the interior of the passage.

In a further aspect of the invention, a bone saw is provided, that includes a flexible saw blade and a shaft. The saw blade is rectangular in shape, has a central longitudinal axis and a cutting edge at its distal tip. The shaft has a central longitudinal axis, and a blade passage within the shaft that houses the saw blade. The blade passage also has a central longitudinal axis, where the central longitudinal axis of the saw blade, of the shaft, and of the blade passage, are parallel.

The bone saw includes a blade opening located at and through a distal end of the shaft and of the blade passage, the blade opening being essentially perpendicular to the longitudinal axis of the shaft. Within the blade passage is a curved abutment that aligns the saw blade with the blade opening. Distal translation of the saw blade within the blade passage causes the saw blade to conform to the curved abutment and exit the blade opening with the cutting edge essentially perpendicular to the longitudinal axis of the shaft.

The bone saw can also include a trunnion at a distal tip of the shaft. The trunnion would be located distal of the blade opening, to facilitate placement of the distal tip of the shaft, to precisely locate a desired blade opening location. The saw blade might further include a longitudinal groove along a side thereof, and the blade opening could further include an indentor penetrating therein. Here, the indentor would be positioned to align with the groove of the saw blade, or would create a groove or indent in the saw blade, as the saw blade exits the blade opening, to facilitate a desired perpendicular blade alignment upon blade exiting of the blade opening.

In one bone saw embodiment, a threaded drive mechanism is included and located at a proximal end of the shaft. The drive mechanism communicates with the saw blade, so that distal advancement of the threaded drive mechanism distally translates the saw blade within the blade passage, causing the cutting edge to exit the blade opening. Additionally, proximally retracting the threaded drive mechanism proximally translates the saw blade within the blade passage, causing the cutting edge to retract into the blade opening. A depth indicator could also be included in one or more embodiments, located at a proximal end of the shaft and communicating with the threaded drive mechanism. The depth indicator would indicate a distance of advancement or retraction of the drive mechanism, the distance being associated with a length of advancing or retracting the cutting edge.

The present invention has the following advantages over currently known methods for treating spinal stenosis:
(1) Normal spine anatomical structures are not disturbed;
(2) Normal muscle attachments to the spine are maintained;
(3) There is diminished chance of unwanted spinal instability;
(4) Less disturbance of the nerves is incurred;
(5) Less scaring around the spinal nerves is incurred;
(6) Spinal decompression is achieved in a more permanent fashion;
(7) The corrective procedure is achieved in a more rapid fashion;
(8) The corrective procedure is achieved with minimal blood loss;
(9) The corrective procedure is achieved with small, percutaneous incisions; and
(10) The corrective procedure is achieved using under local anesthesia.

BRIEF DESCRIPTION OF THE DRAWINGS

The drawings herein are included for the purpose of illustrating preferred embodiments of the present inventions; however, it should be realized that the invention is not limited to the precise arrangements and/or sequence of steps shown.

FIGS. 1A, 1B and 1C illustrate a lower or distal shell portion of a pedicle lengthening implant, in accordance with one preferred embodiment of the invention;

FIGS. 2A1, 2A2, 2B1, 2B2, 2C1, 2C2, 2D1 and 2D2 illustrate components of the distal or lower shell, in top and cross-sectional views, including the shell with inner channels, a floating nut and a retaining washer;

FIGS. 4A, 4B, 4C and 4D illustrate an expanding portion of an upper or proximal portion of the pedicle lengthening implant in multiple perspective views, in accordance with one preferred embodiment of the invention;

FIGS. 5A, 5B and 5C illustrate a threaded portion of the upper or proximal portion of the implant in top, side and cross-sectional views, in accordance with one preferred embodiment of the invention;

FIGS. 6A, 6B, 6C and 6D illustrate the threaded portion of the upper portion in a multiplicity of perspective views;

FIGS. 7A1, 7A2, 7B1, 7B2, 7C, 7D, 7E and 7F illustrate components and assembly of the upper portion of the implant;

FIGS. 8A1, 8A2, 8B1, 8B2, 8C1, 8C2, 8D1 and 8D2 illustrate the upper or proximal portion in a multiplicity of top and cross-sectional views;

FIGS. 9A, 9B and 9C illustrate the upper implant portion in a multiplicity of perspective views;

FIGS. 10A1, 10A2, 10B1, 10B2, 10C1, 10C2, 10D1, 10D2 illustrate the function of the floating nut within the lower implant portion to accommodate offset between the upper and the lower portions of the implant;

FIGS. 11A, 11B and 11C illustrate the entire pedicle lengthening implant (distal and proximal portions, along with jack screw and locking bolt) in a multiplicity of exploded and cross-sectional views;

FIGS. 15A, 15B, 15C, 15D and 15E illustrate a radial saw in cross-section and a multiplicity of working end views, in accordance with another preferred embodiment of the invention;

FIGS. 30A, 30B and 30C illustrate a cross-sectional view of a vertebrae undergoing insertion of a locking bolt to lock or fasten the upper and lower portions of the implant together, and to secure the lengthened state of the pedicle and the expanded state of the spinal canal.

DETAILED DESCRIPTION OF THE ILLUSTRATED EMBODIMENTS

Figure 3B:
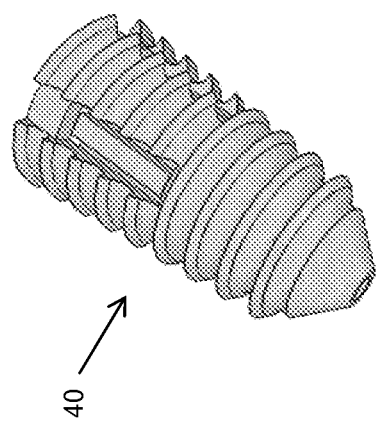
FIGS. 3A and 3B illustrate the components of the lower shell of the implant in exploded and assembled perspective views.

Referring now to the drawings, where like numerals indicate like elements, there is shown in FIGS. 1A-1C, a top view 1A, side view 1B, and cross-sectional view 1C, of a lower or distal shell portion 10 of a pedicle lengthening implant of the present invention. The lower implant shell 10 has outer threads 2 and hollow inner spaces 8, 12, along with side wall slots 4 and a cannulation hole 6.

FIGS. 2A1-2D2 comprises lower implant components, including the lower implant shell 10, a floating nut 20 and a locking ring 30. The locking ring 30 is shown in cross-section, and by top view, in FIGS. 2A1 and 2A2, respectively. The locking ring 30 comprises a substantially circular shape and has a central passage 22. The floating nut 20 is shown in cross-section and by top view in FIGS. 2B1 and 2B2, respectively. The floating nut 20 contains a plurality of flanges 18 on its' outer surface, and a tapered entrance 16 to an inner threaded portion 14.

An assembled lower implant portion 40 is shown in cross section and by top view in FIGS. 2D1 and 2D2, respectively. When assembled, the floating nut 20 fits loosely into the space 8 of the outer shell 10, while the locking ring 30 is substantially press fit, or otherwise secured into the space 12 of the lower implant shell 10. Notice that the locking ring 30 secures the floating nut 20 within the outer shell 10, but allows the floating nut 20 to move in a substantially side to side direction (perpendicular to the long axis of the lower implant shell 10) within the space 8, while the outer flanges 18 of the floating nut 20 are loosely confined within the side wall slots 4 of the outer implant shell 10 to prevent rotation of floating nut 20 during the threadable insertion of a locking bolt (described later).

Figure 3A:
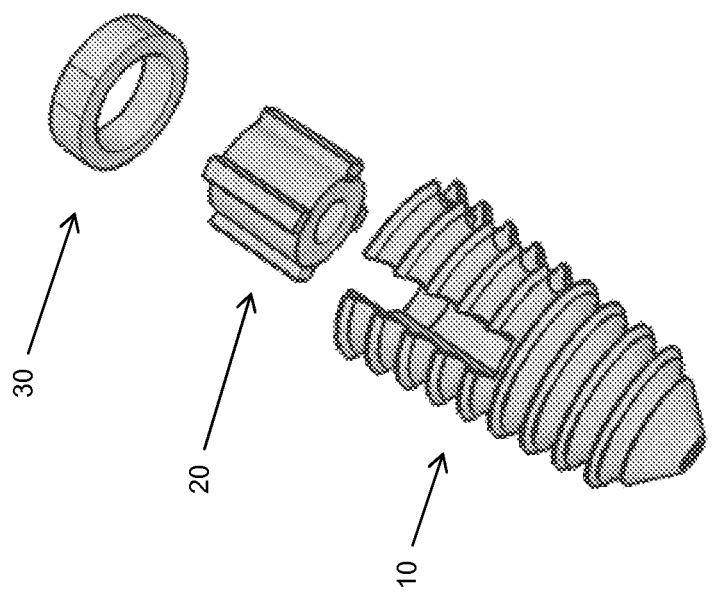

FIGS. 3A-3B illustrate the assembled lower or distal implant portion 40 in perspective exploded view, FIG. 3A, and perspective assembled view FIG. 3B. The exploded view FIG. 3A shows the relationship of the locking ring 30, the floating nut 20 and the lower implant shell 10 in one preferred embodiment, while FIG. 3B shows a perspective view of the assembled lower implant 40.

FIGS. 4A-4D illustrate an expanding portion 50 of upper or proximal implant 60 in a plurality of perspective views. The expanding portion 50 is substantially cylindrical in shape and comprises a plurality of slots 32 in its' side walls that divide the cylindrical walls into flange-like projections 24. The base 34 of the expanding portion 50 of the upper implant 60 contains an opening 38 for the passage of a locking bolt (described later).

In this embodiment, the side wall flanges 24 are shown to have a bore 26 for the secure attachment of a plurality of guide pins 54 (shown in FIG. 12) that connect and guide the expanding portion 50 and the threaded portion 70 (shown in FIGS. 5A-5C) of the upper implant 60 (shown in FIG. 8) together. In addition, the expanding portion 50 of upper implant 60 contains holes 28 for hinge pins 110 (shown in FIGS. 7 and 9) used to moveably connect the hinged flanges 100 (FIGS. 7 and 9) to the expanding portion 50 of the upper implant 60.

FIGS. 5A-5C illustrate a threaded portion 70 of the upper or proximal portion 60 of the implant, as shown in side view in FIG. 5A, cross-sectional view in FIG. 5B, and top view in FIG. 5C. In the presently shown embodiment, the threaded portion 70 of the upper implant portion 60 has outer threads 42, side slots 52, and a threaded inner passage 58. A gliding hole 56, shown at the base of each slot 52, allows for the slidable passage of guide pins 54 therein (shown in FIG. 12), to slidably connect the threaded portion 70 to the expanding portion 50 (FIG. 4) of the upper or distal implant 50 (FIGS. 7-9 and 11, 12).

FIGS. 6A-6D illustrate a threaded portion 70 of the upper implant 60 in perspective view in FIGS. 6A and 6C, a bottom view in FIG. 6B, and a top view FIG. 6C. A threaded outer surface 42 can be appreciated on the threaded portion 70 of the upper implant 60, for threadable introduction into a bone bore or passage in the pedicle. The threaded portion 70 of the upper or proximal implant 60 contains an inner threaded passage 58 with threads 44 on its side walls threadable insertion of a jack screw 80 (FIG. 7). The threaded upper portion 70 further contains side wall slots 52, with gliding holes 56 at the base of each slot 52, wherein guide pins 54 (FIG. 12) are passed for slidable attachment of the threadable 70 and expanding 50 portions of the upper or proximal implant 60. The threaded portion 70 of the upper implant 60 is also shown to contain holes for hinge pins 48, used to connect hinged flanges 90 (FIGS. 7 and 9) that can fit partially into slots 46 on the bottom surface of the threaded portion 70 of the upper implant 60.

FIGS. 7A1-7D illustrate multiple cross-sectional views of upper implant 60. The upper implant 60 is comprised of the threaded portion 70 and the expanding portion 50, along with jack screw 80, guide pins 54 (FIG. 12), and expandable flanges 90, 100. In FIG.7A1-7A2, the plane of the cross-section is designated by line A-A 76 shown in FIG. 7E. The expandable flanges 90 in this plane are shown to hinge on the expanding portion 50 of the upper implant 60.

In FIG. 7B1-7D, the plane of cross-section is designated by line B-B 77 in FIG. 7F, which is substantially at a right angle to line A-A 76 in FIG. 7E. The expandable flanges 100 in this plane are hinged on the threaded portion 70 of the upper implant 60.

When assembled in the unlengthened state, the threaded portion 70 of the upper implant 60 is positioned just above the expanding portion 50 of the upper implant 60, leaving an inner passage 58 through which the jack screw 80 can be threaded. Further, note that the jack screw 80 can be partially threaded into the inner threaded passage 58 of the threaded portion 70 of the upper implant 60, with both sets of expanding flanges 90, 100 remaining hinged into the confines of the expanding portion 50 of the upper implant 60. However, from this state, further threadable insertion of the jack screw 80 (as shown in FIG. 7C) causes the expandable flanges 90 to hinge outward, so that the flange projections 66 extend substantially outside the confines of the expanding portion 50 of the upper implant 60. Note that the length of the upper implant 60, with flanges radially extended as shown in FIG. 7C, remains unchanged from the length of the upper implant portion 60 shown in FIGS. 7A and 7B.

With further threadable insertion of the jack screw 80, as shown in FIG. 7D, the overall length of the upper implant 60 increases (lengthened state of the upper implant 60) as the jack screw 80 contacts the base 34 of the expanding portion 50 of the upper implant 60, and pushes the expandable portion 50 away from the threaded portion 70, causing an overall lengthening of the upper or proximal implant portion 60. It should be apparent to one skilled in the art that the overall length of the upper implant 60 is greater in FIG. 7D, compared to the length of the upper implant 60 in FIGS. 7A, 7B and 7C.

FIGS. 8A1-8D2 illustrate an upper implant 60 in its unlengthened (FIGS. 8A2, 8B2 and 8C2) and lengthened (FIG. 8D2) states. FIGS. 8A1, 8B1, 8C1 and 8D1 show top views of the threaded portion 70 of the upper implant 60 with various planes of cross-section, demarcated by lines A-A 76, B-B 77 and C-D 79, used to illustrate the planes of cross-section shown in corresponding FIGS. 8A2, 8B2, 8C2 and 8D2 directly below.

FIGS. 8A1 and 8A2 show a top view and a cross-sectional view, respectively, of the upper implant 60 along line A-A 76. In FIG. 8A2, the hinged flanges 90 are shown to hinge on the threaded upper portion 70, while the jack screw 80 is shown threadably inserted to a level of contact with the base 34, but without substantially pushing the base 34 of the expanding portion 50 of the upper implant 60 away from the threaded portion 70 of the upper implant 60.

FIGS. 8B1 and 8B2 show a top view and a cross-sectional view, respectively, of the upper implant 60 along line B-B 77. In FIG. 8B2, the hinged flanges 100 are shown to hinge on the slidable portion 50, allowing the hinged flanges 100 to move with the expanding portion 50 as the jack screw 80 pushes the expanding portion 50 away from the upper threaded portion 70.

FIGS. 8C1 and 8C2 show the upper implant 60 in a top view and cross-sectional view, respectively, along line C-D 79. In this view, the hinged flanges 90, 100 are respectively attached to the threaded upper portion 70 and the expanding portion 50 of the upper implant 60, although in the unlengthened state, the flange projections 66 are at substantially the same level.

FIGS. 8D1 and 8D2 show a top view and a cross-sectional view, respectively, of the upper implant 60 in the lengthened state, with the plane of cross section illustrated by line C-D 79. In this view, the jack screw 80 has been threadably inserted further into the threaded portion 70 of the upper implant 60, and has pushed against the base 34 of the expanding portion 50 of the upper implant 60, resulting in an overall lengthening of the upper implant portion 60. In the lengthened state, as shown in FIG. 8D2, it should be apparent that the flange projections 66 lie at different levels, with a vertical gap 74 between the levels of respective flange projections 66.

FIGS. 9A-9C illustrate one preferred embodiment of the invention, showing the upper implant 60 in three different perspective views (all in the unlengthened state). The threaded portion 70 has exterior threads 42, and is shown substantially in contact with the expanding portion 50 of the upper implant portion 60. The flange projections 66 are shown to project outside a diameter of the expanding portion 50, as a result of the jack screw 80 being threadably inserted into the threaded portion 70 of the upper implant 60.

FIGS. 10A1-10D2 illustrate a novel mechanism for accommodating lateral offset (translational malalignment) between the upper 60 and lower 40 portions of the pedicle lengthening implant or device 150 that may occur during the lengthening process. In FIGS. 10A1, 10B1, 10C1 and 10D1, the upper 60 and lower 40 implant portions are represented in cross-section with the central axis of the upper implant portion 60 shown as line 68 and the central axis of the lower implant portion 40 shown as line 72. A space 74, between the upper 60 and lower 40 implant portions, represents a gap created by lengthening of the upper implant portion 60, as would be done during a pedicle lengthening procedure.

In the event the central axis of the upper 60 and lower 40 implant portions should be offset (translationally malaligned), the floating nut 20 (FIGS. 10A2, 10B2, 10C2 and 10D2) is able to shift in position, so that locking bolt 120 (FIGS. 11 and 12) is able to secure the upper portion 60 to the lower portion 40 in the offset position. FIGS. 10A-10D illustrate progressive amounts of offset between the central axis of the upper 60 and the lower 40 implants, and progressive lateral shift of the floating nut 20, within the space 8 of the lower implant shell 10, to accommodate the offset.

FIGS. 11A-11C illustrate cross-sectional views of a preferred embodiment of the pedicle lengthening device 150 (in an exploded cross-sectional view in FIG. 11A, and an assembled cross-sectional view in FIGS. 11B and 11C). The planes of the cross-section are illustrated by lines A-A 76 and B-B 77, respectively. FIG. 11A shows the lower implant portion 40, the upper implant portion 60 (in the lengthened state), and the locking bolt 120.

The lower implant portion 40 is shown to contain the floating nut 20 and the retaining washer 30. The upper implant portion 60 has a threaded portion 70, an expanding portion 50, and incorporates an internal jack screw 80 shown threaded into the upper implant portion 60 such that the base 34 of the expanding portion 50 is pushed away from the threaded portion 70, resulting in an overall lengthening of the upper implant portion 60 (lengthened state).

The locking bolt 120 comprises a threaded tip 78, shaft 84 and drive mechanism 82. FIG. 11B shows an assembled pedicle lengthening device 150 in cross-section along a plane illustrated by line A-A 76. The pedicle lengthening device 150 is shown to contain a jack screw 80 threaded inward to cause a lengthening of the upper implant portion 60 by a distance 74. The locking bolt 120 is shown to pass through a central region of the jack screw 80, and to threadably attach to the floating nut 20, to fasten the upper 60 and the lower 40 portions of the implant 150 securely together.

FIG. 11C shows the pedicle lengthening device 150, in cross-section along line B-B 77. In this cross-sectional plane, the expandable flanges 100 are shown to hinge on the expanding portion 50 of the upper implant 60. As this view illustrates, the lengthened state of the implant 150 presents a gap 75 between the threaded 70 and the expanding 50 portions of the upper implant 60 due to the action of the jack screw 80 pushing the expanding portion 50 of the upper implant 60 away from the threaded portion 70 of the upper implant 60.

Figure 12:
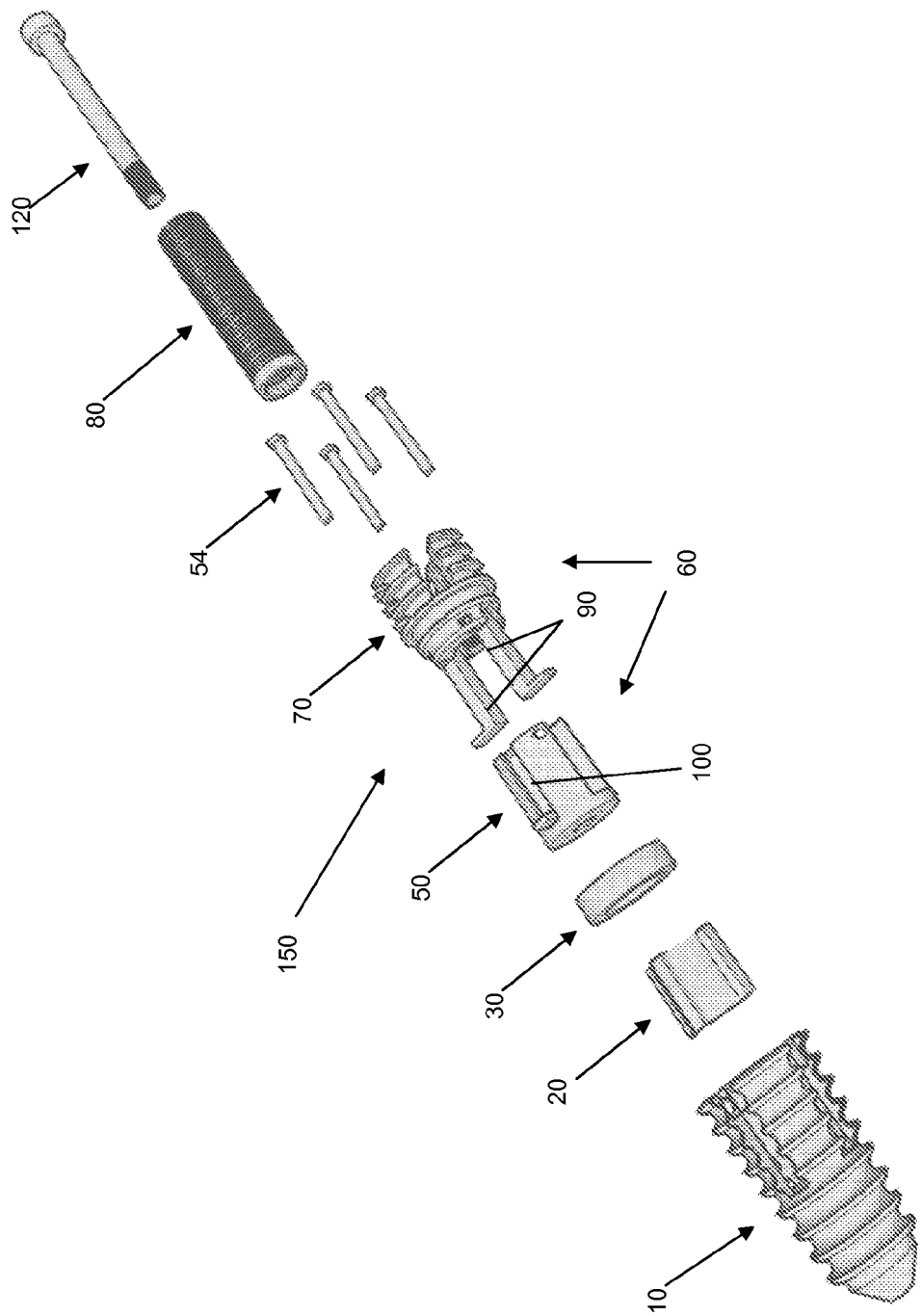
FIG. 12 illustrates the entire implant (distal and proximal portions) in an exploded, perspective view.

FIG. 12 illustrates an exploded perspective view of the pedicle lengthening device 150. In this illustration, the relationship of the various components of this preferred embodiment can be appreciated. The lower implant shell 10 is shown to contain the floating nut 20 and the locking ring or retaining washer 30. The expanding portion 50 of the upper implant 60 is shown to have a pair of attached expandable flanges 100. The threaded portion 70 of the upper implant 60 also has a pair of expandable flanges 90 which are oriented at substantially different positions than the expandable flanges 100 of the expanding portion 50 of the upper implant 60. The expanding 50 and the threaded 70 portions of the upper implant 60 are attached by guide pins 54 which allow the threaded 70 and the expanding 50 portions of the upper implant 60 to move apart from one another (resulting in a lengthening of the upper implant 60) in a direction substantially parallel to the longitudinal axis of the pedicle lengthening implant or device 150, but to remain in alignment along the longitudinal axis. The jack screw 80 is shown to have a hollow interior, allowing the locking bolt 120 to pass there through, and thread into the floating nut 20 to secure or lock the entire implant 150 together following implantation.

FIGS. 13A-13E illustrate a preferred embodiment of a novel linear bone saw. FIG. 13A illustrates a saw blade 94 manufactured from a flexible material, such as stainless steel, titanium, nitinol, cobalt chromium alloy, tantalum, or a polymeric or composite material. The saw blade 94 includes a cutting edge or tip 108 and attachment holes 111, or other attachment means, to allow fastening to the saw 140.

FIG. 13B shows a cross-sectional view of the linear saw 140, including a shaft 107, a body 105, and a handle 123. The body 105 of the saw 140 contains a blade holding mechanism 115, securing the saw blade 94 via the attachment holes 111. The blade 94 is shown to pass down a blade passage 101 within the shaft 107. The blade passage 101 is substantially parallel to the longitudinal axis of the saw 140, until reaching a curved region 97 within the blade passage 101, and exiting the shaft 107 at a blade opening 99 located on the side of a distal end of the shaft 107.

The blade 94 is attached to a threaded drive mechanism 121, which can be threadably advanced or withdrawn within the body 105 of the saw 140 by turning a knob 127. The saw 140 includes a depth indicator 125 that indicates a distance the cutting edge or tip 108 protrudes from blade opening 99. The shaft 107 of the saw 140 includes a trunnion 128 on the cutting or distal end of the shaft 107 for engagement with the lower implant portion 40 (FIGS. 1-3) during cutting.

FIG. 13C shows an end view of the cutting or distal end of the saw 140, illustrating the shaft 107 and trunnion 128. FIG. 13D shows a cross-sectional view of the saw 140, with the blade 94 extending from the blade opening 99. Note that in comparison to FIG. 13B, the blade 94 has been advanced so that it protrudes from the side of the shaft 107, and that the threaded drive mechanism 121 has been threaded distally deeper into the body 105 of the saw 140. Also, note that the depth indicator 125 protrudes above the knob 127, to reveal the distance the cutting edge 108 of the blade 94 protrudes from the blade opening 99.

FIG. 13E illustrates an end view of the cutting end of saw 140 with the blade 94 protruding, as in FIG. 13D. The shaft 107 and trunnion 128 are shown, and blade 94 is shown protruding from the side of the shaft 107, with the cutting edge or tip 108 pointed away, or perpendicular, from the central, longitudinal axis of the saw 140.

Figure 13:
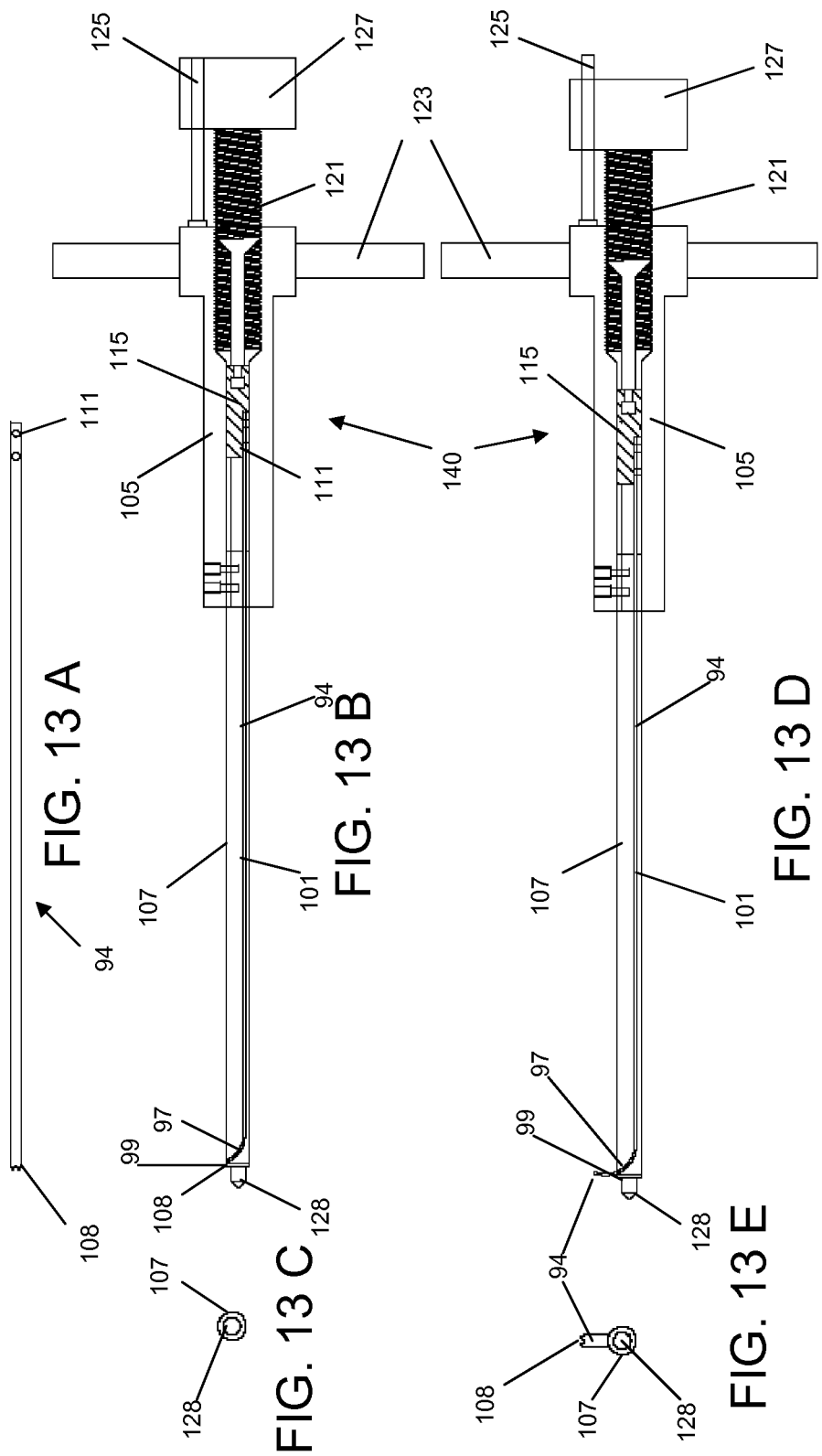
FIGS. 13A, 13B, 13C, 13D and 13E illustrate a linear saw in cross-section, with accompanying front views, in accordance with one preferred embodiment of the invention.
Figure 14:
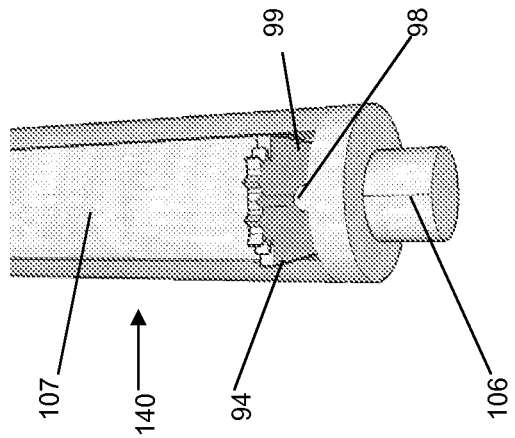
FIGS. 14A and 14B illustrate a cutting end of a saw blade of the linear saw.
Figure 14:
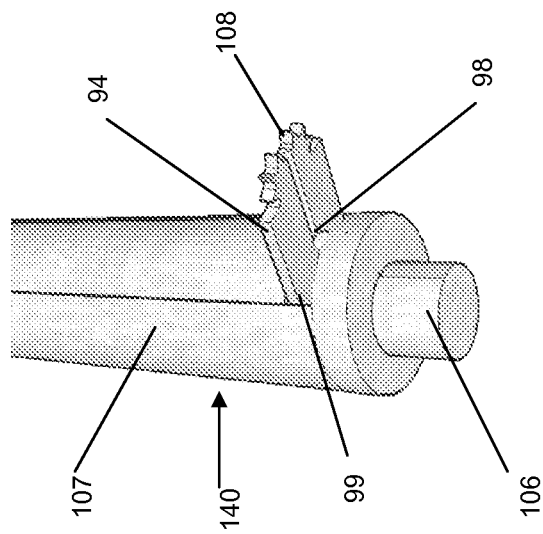

FIGS. 14A - 14B illustrate the cutting or distal end of the linear bone saw 140 in two perspective views. As shown in FIGS. 13B and 13D, the saw 140 includes a shaft 107 with a trunnion 106 at the distal end of the shaft 107, designed to engage the lower implant portion 40 (FIGS. 1-3). A blade opening 99 is located at a substantially perpendicular angle to the longitudinal axis of the linear saw 140. The flexible blade 94 is shown having the cutting edge 108 protruding from the blade opening 99. Blade opening 99 includes an indentor 98, which is a raised portion designed to introduce a crimp or counter bend to the flexible saw blade 94, which serves to counteract a curling of the blade 94 possibly produced by a passing of the flexible blade 94 through the curved portion 97 of the blade passage 101 (FIGS. 13A and 13C). Alternatively, a groove could be pre-manufactured into the flexible saw blade 94, with the indentor 98 positioned to align with the groove of the saw blade 94 as the saw blade exits the blade opening 99, thereby facilitating desired perpendicular blade 94 alignment upon exiting the blade opening 99.

FIGS. 15A - 15E illustrate a preferred embodiment of a radial bone saw 130. The radial saw 130 includes a handle 132 and a shaft 113. Internally, the radial saw 130 has a drive shaft 116 attached to a saw blade 96 on a cutting or distal end of the saw 130. The drive shaft 116 is also attached to an offset rotation knob 118 on the non-cutting or proximal end of the saw 130.

A trunnion 128, for alignment with the lower implant portion 40 (FIGS. 1-3), is also located on the cutting end of the saw 130. A cannulation passage 114 is shown to pass through a central region of the longitudinal axis of the saw 130, so that the saw 130 can be placed over a guide wire.

FIGS. 15B, 15C and 15D illustrate the cutting or distal end of the saw 130 in an end, cross-sectional view at the level (or location) of the blade opening 102. In FIG. 15B, the saw blade 96 is shown attached to the drive shaft 116. Note that the drive shaft 116 is located towards a periphery of the cross-section of the shaft 113. In FIG. 15B, the blade 96 is shown contained within the shaft 113, and a central cannulation hole 114 is shown along a central axis of the shaft 113 so that the saw 130 can be placed over a guide wire. FIG. 15C illustrates the blade 96 partially protruding from the shaft 113 due to the rotational movement of the drive shaft 116. FIG. 15D shows the blade 96 fully protruding from the shaft 113. The blade 96 has a cutting surface 112 oriented away from a central axis of the shaft 113, and has a cut away region 119 so that the blade does not cover the cannulation hole 114 when the blade is contained within the shaft 113. FIG. 15E shows an end view of the non-cutting or proximal end of the radial saw 130. The rotation knob 118 has a central axis substantially offset from the handle 132. The rotation knob 118 also has a semicircular slot 117 to allow passage of a guide wire in all rotational positions of rotation knob 118. The rotation knob 118 also attaches to the drive shaft 116 and deploys the blade 96 by its rotation relative to the saw handle 132.

Figure 16:
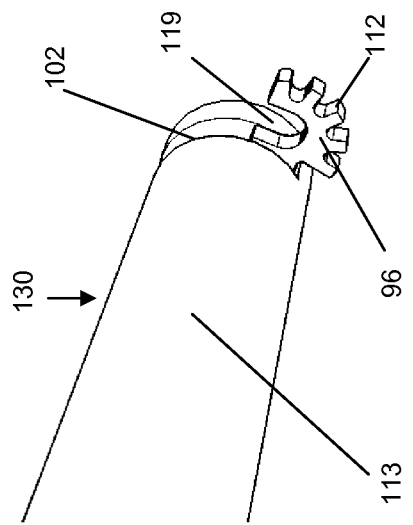
FIGS. 16A and 16B illustrate a cutting end of the radial saw.
Figure 16:
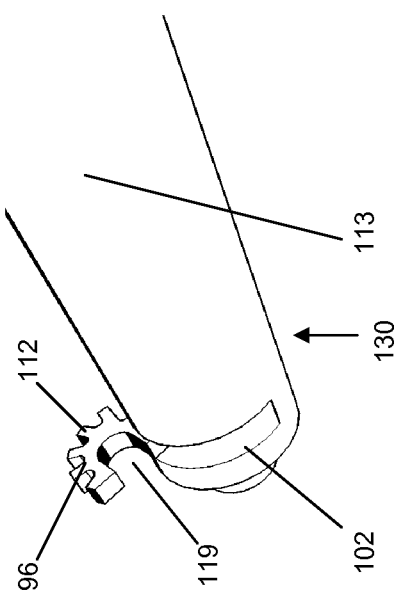

FIGS. 16A and 16B illustrate the cutting or distal end of the radial saw 130 in two perspective views. The saw 130 has a shaft 113 with an opening 102 for the blade 96 to protrude or deploy outward from within the shaft 113. The blade 96 is shown to comprise a cutting surface 112 and a cut away region 119 for the passage of a guide wire.

Figure 17:
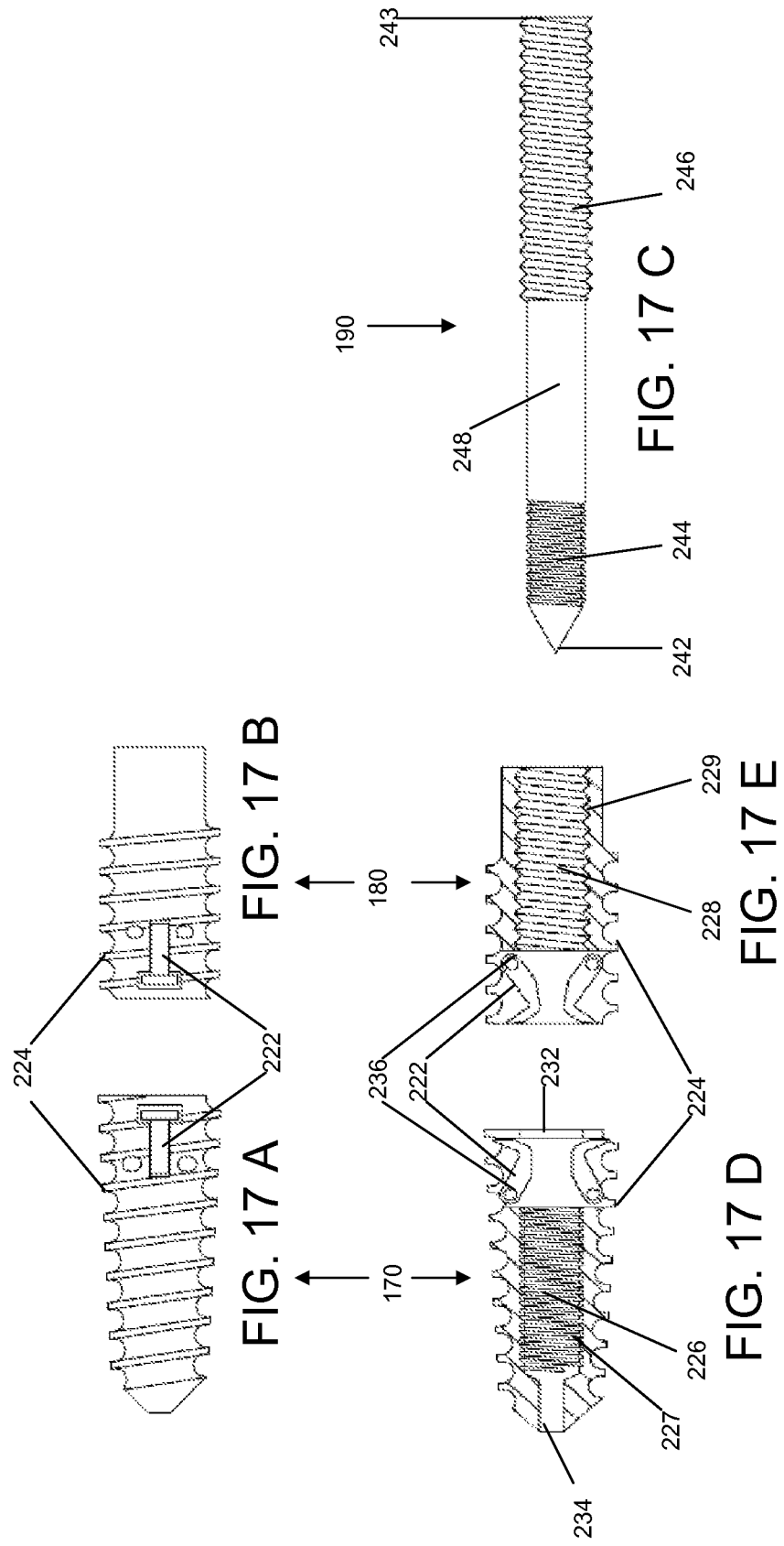
FIGS. 17A, 17B, 17C, 17D and 17E illustrate lower (distal) and upper (proximal) portions of a dual pitch pedicle lengthening implant, in accordance with another preferred embodiment of the invention.
Figure 18:
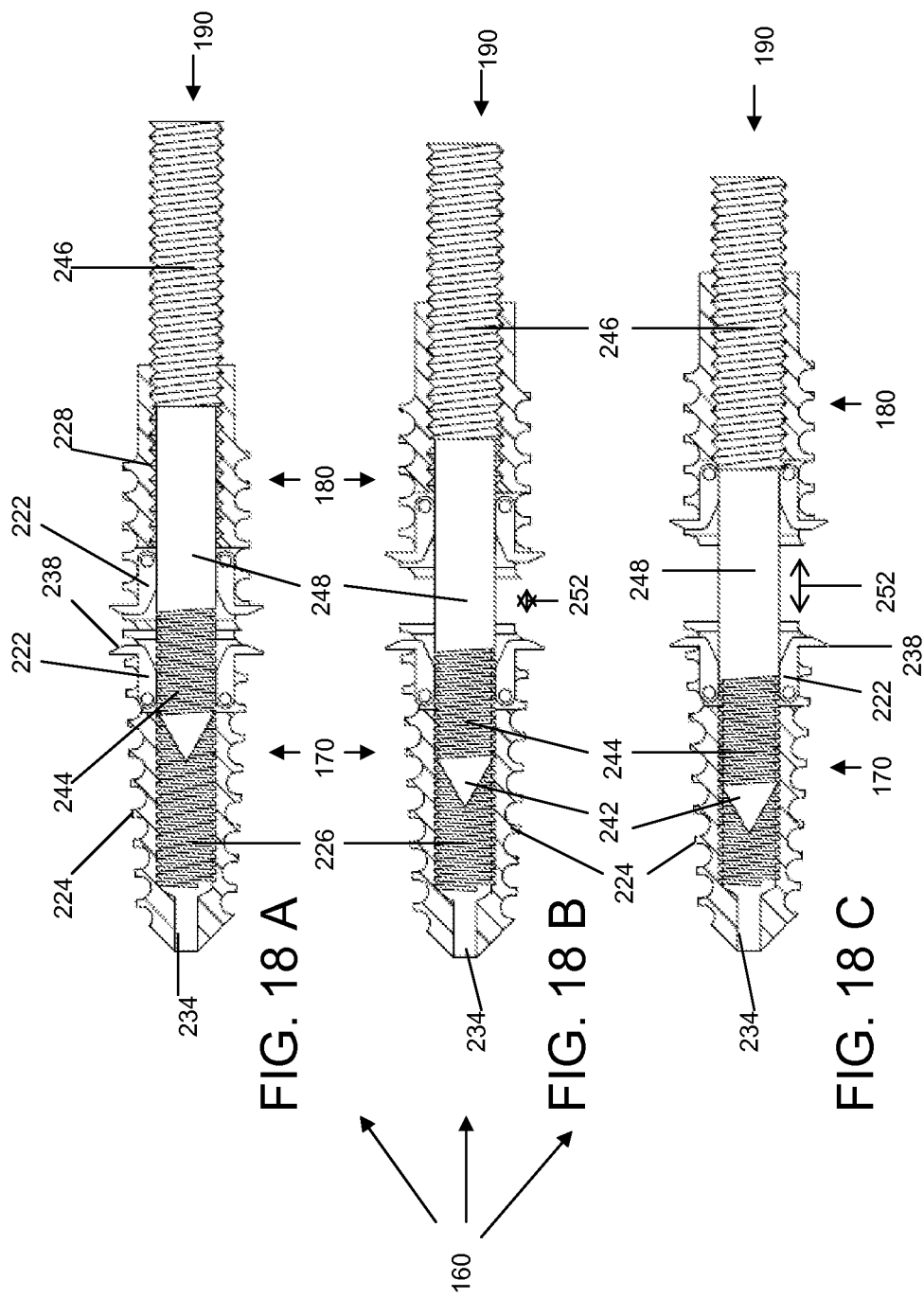
FIGS. 18A, 18B and 18C illustrate cross-sectional views of the dual pitch implant in various working states.

FIGS. 17 and 18 illustrate an alternate preferred embodiment of a pedicle lengthening device or implant 160. FIGS. 17A-17E illustrate components of the alternate preferred embodiment. FIG. 17A shows a base section or proximal portion 170 of the alternate device in a side view and FIG. 17D illustrates the proximal portion or base section 170 in a cross-sectional view. The base section 170 has outer threads 224 and an inner threaded passage 226 having inner threads 227. A distal end of the base section 170 contains an optional cannulation hole 234, allowing the device to be placed over a guide wire.

The base section 170 also includes a plurality of hinged flanges 222 attached through a hinge mechanism 236 to the base section 170. These optional hinged flanges 222 on the base section 170 are designed to improve the bony purchase of the base section 170 to the vertebral bone from within the passage. In addition, the base section 170 is shown to contain a close tolerance bore 232 for the passage of the inner bolt (FIG. 17C).

FIGS. 17B and 17E illustrate a side view and cross-sectional view, respectively, of the upper section or proximal portion 180 of the alternate preferred embodiment of the pedicle lengthening device or implant 160. The upper section 180 has outer threads 224 and an inner threaded passage 228 comprising inner threads 229. The upper section or proximal portion 180 can also include a plurality of flanges 222 hinged on the upper section through a hinge mechanism 236. The purpose of the hinged flanges 222 on the upper section 222 is to grip the bone at the site of the pedicle cut.

FIG. 17C illustrates an inner bolt 190 comprising a shaft 248, a distal tip 242, and a drive mechanism 243 at a proximal end providing threadable insertion of the inner bolt 190. The inner bolt 190 also includes a plurality of threaded sections 244, 246 for engagement with the base section or distal portion 170 and the upper section or proximal portion 180, respectively, of the pedicle lengthening device. It should be appreciated by one skilled in the art that the pitch of the threads 244 on the distal portion of the inner bolt 190 are substantially smaller than the pitch of the threads 246 on the proximal end of the inner bolt 190. The smaller pitch distal threads 244 are substantially similar to the pitch of the inner threads 227 of the base section 170, while the larger pitch proximal threads 246 of the inner bolt 190 are substantially similar to the threads 228 of the upper section 180.

FIGS. 18A, 18B and 18C illustrate the function of the alternate preferred embodiment of the pedicle lengthening device or implant 160. In FIG. 18A, the base section 170 and upper section 180 are in substantial contact, and the inner bolt 190 is partially threaded into the inner threaded passage 226 of the base section 170. In FIG. 18A, the inner bolt 190 is shown to have caused the hinged flanges 222 on both the base section 170 and the upper section 180 to be pushed outward (compared to FIG. 17), such that a portion of the hinged flanges 222 projects beyond the outer thread 224 of the base 170 and of the upper section 180.

FIG. 18B illustrates the effect of deeper threaded insertion of the inner bolt 190 into the upper section 180 and the base section 170. The inward threading of the inner bolt 190 has caused the upper section 180 to be drawn away from the base section 170 as a result of the larger pitch threads 246 within the upper section 180 relative to the smaller pitch threads 244 of the base section 170. The further inward threading of the inner bolt 190 has resulted in the formation of a gap 252 between the base 170 and the upper 180 sections.

FIG. 18C illustrates the effect of further threaded insertion of the inner bolt 190. Deeper, more distal, insertion of the inner bolt 190 results in a further widening of the gap 252 between the upper 180 and the base sections 170 of the pedicle lengthening device 160.

Figure 19:
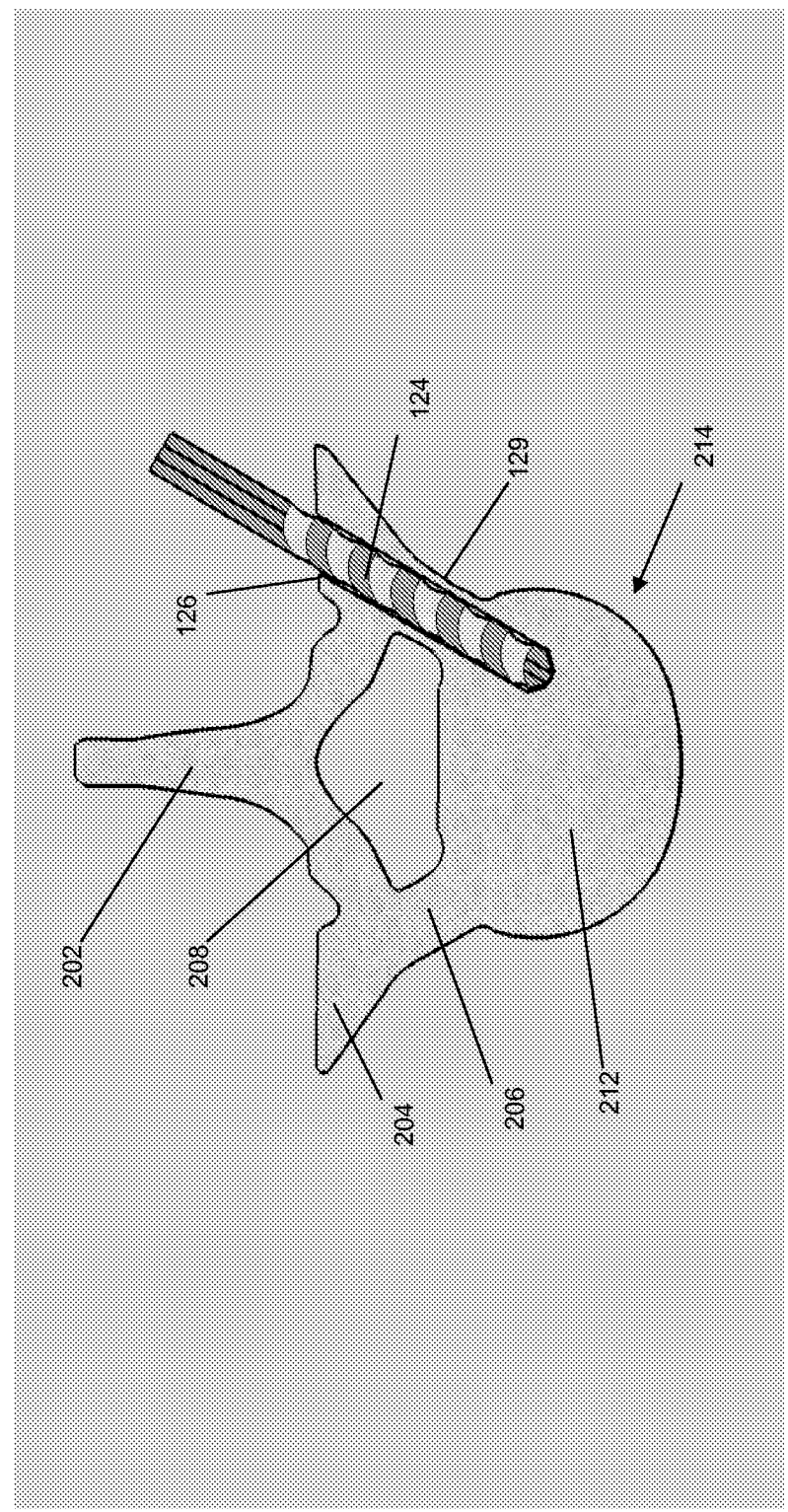
FIG. 19 illustrates a cross-sectional view of a vertebrae undergoing drilling of a pedicle bore along a long axis of one pedicle.

FIGS. 19-31 illustrate a preferred sequence of steps for performing pedicle lengthening in accordance with the present invention. FIG. 19 illustrates a cross-sectional view of a vertebra 214 having a vertebral body 212, a pedicle 206, a transverse process 204, a spinous process 202, and a spinal canal 208. A cannulated drill 124 is shown forming a pedicle bore 126 through a central region of the pedicle 206.

Figure 20:
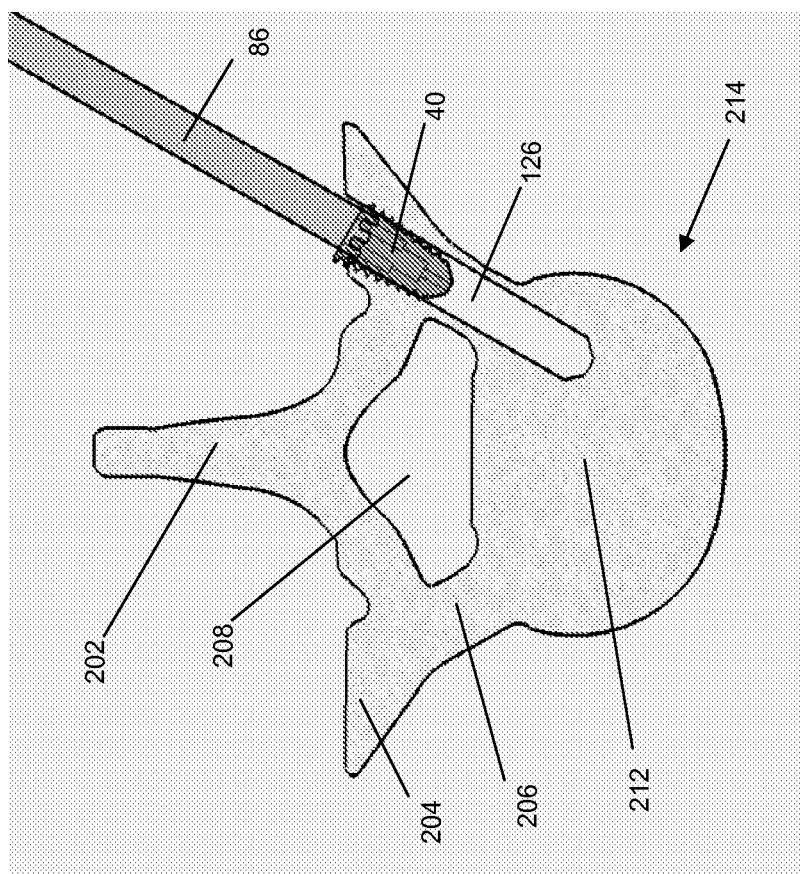
FIG. 20 illustrates a cross-sectional view of a vertebrae undergoing insertion of the distal or lower portion of the pedicle lengthening implant into the pedicle passage or bore, in accordance with one preferred embodiment of the invention.

FIG. 20 shows a vertebra 214 after the pedicle bore 126 is formed. The lower implant portion 40 is shown undergoing threadable insertion into the pedicle bore 126 using an insertion tool 86.

FIGS. 21A-21B again show a vertebra 214 with the lower implant portion 40 seated at the base of the pedicle bore 126 (FIG. 20). Note that the top of the lower implant portion 40 is positioned substantially at a junction between the pedicle 206 and the vertebral body 212.

Figure 22:
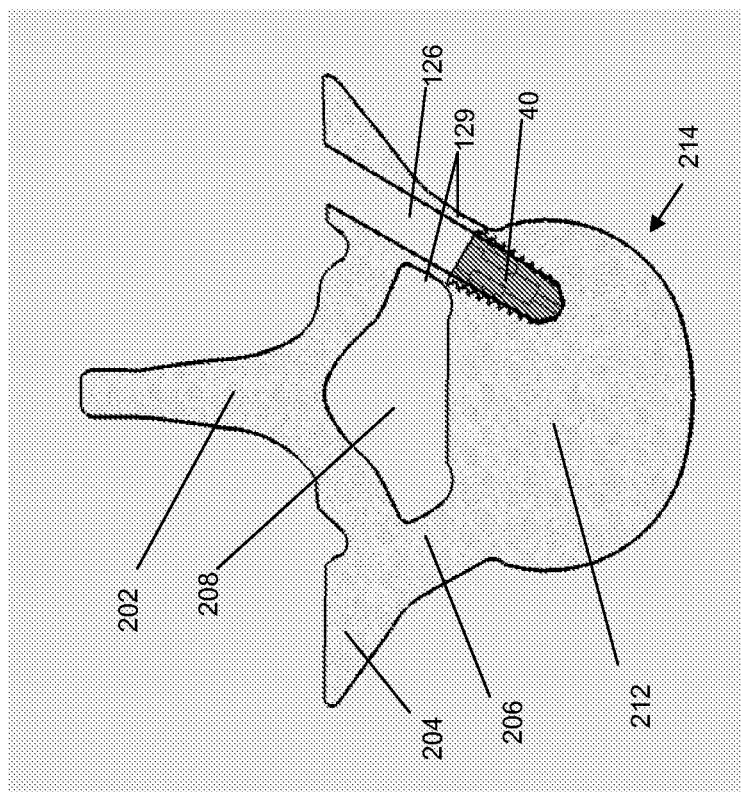
FIG. 22 illustrates a cross-sectional view of a vertebrae following seating of the lower implant into the bottom of the pedicle bore.

FIG. 22 illustrates the vertebra 214 after insertion of the lower implant portion 40 at the base of the pedicle bore 126. Again, the upper surface, or proximal end, of the lower implant portion 40 is shown positioned at the junction of the pedicle 206 and the vertebral body 212.

FIGS. 23A and 23B illustrate a vertebra 214 undergoing cutting of the pedicle 206 with a pedicle saw 140. The saw 140 is shown cutting the bone of the lateral wall of the pedicle 206 from inside the pedicle passage or bore 126. Note that the pedicle saw 140 is positioned substantially in contact with the lower implant 40 to properly align the pedicle cut with the pedicle lengthening device.

Figure 24:
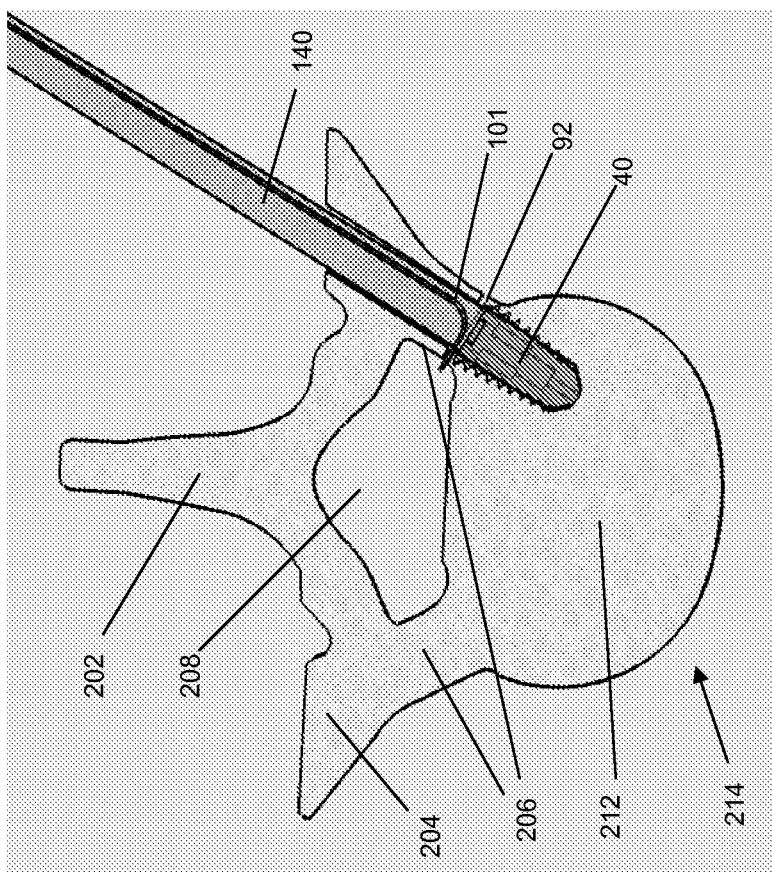
FIG. 24 illustrates a cross-sectional view of a vertebrae undergoing cutting of a medial portion of the pedicle wall using the linear pedicle saw.

FIG. 24 illustrates a vertebra 214 undergoing the completion of cutting of the pedicle 206. The saw 140 is shown cutting the bone of the medial wall of the pedicle 206 to complete a circumferential transection of the pedicle 206, leaving bone cut 92 at the junction of the pedicle 206 and the vertebral body 212.

Figure 25:
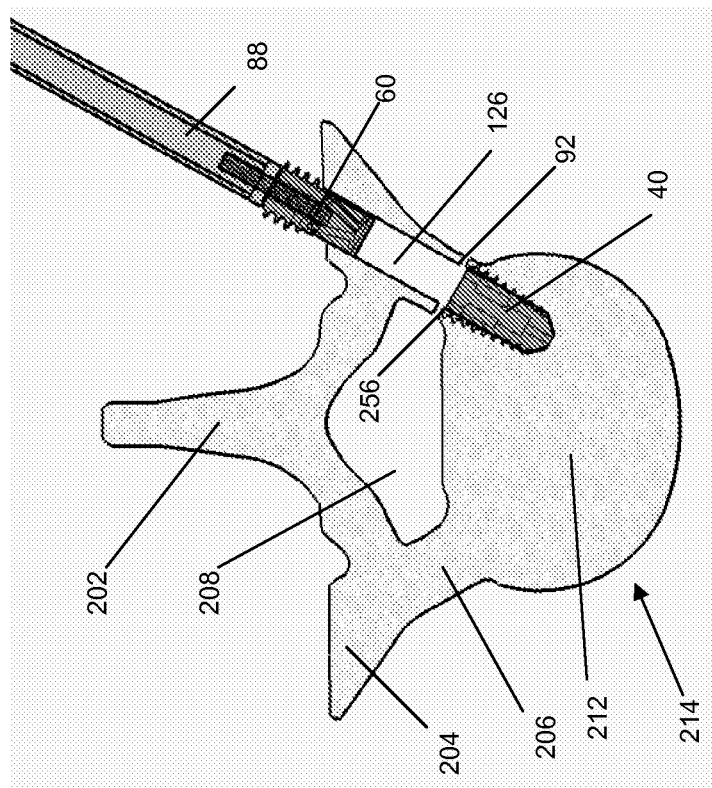
FIG. 25 illustrates a cross-sectional view of a vertebrae undergoing initial insertion of an upper portion of the pedicle lengthening implant, in accordance with one preferred embodiment of the invention.

FIG. 25 illustrates a vertebrae 214 following completion of the pedicle cut 92. An upper implant portion 60 is shown at a beginning of threadable insertion into the pedicle bore 126.

Figure 26:
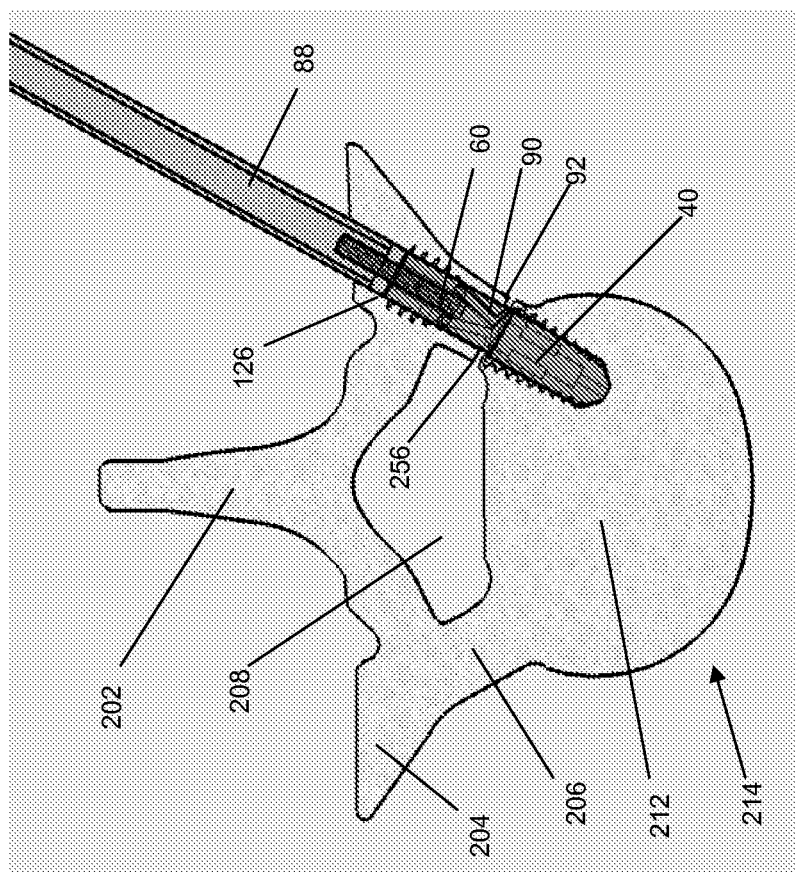
FIG. 26 illustrates a cross-sectional view of a vertebrae undergoing final seating of the upper or proximal portion of the implant into the pedicle bore.

FIG. 26 illustrates a vertebra 214 with the upper implant 60 seated within the pedicle bore 126 to the point where it comes into substantial contact with the lower implant 40.

Figure 27:
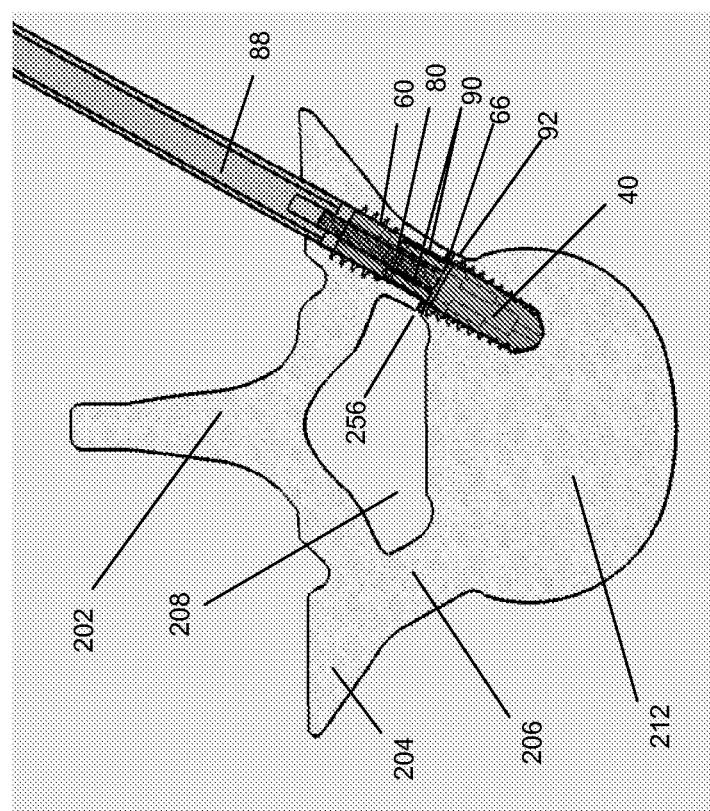
FIG. 27 illustrates a cross-sectional view of a vertebrae following deployment of expandable flanges from the upper portion of the implant.

FIG. 27 illustrates a vertebra 214 following deployment of the expandable flanges 90 which have projected (hinged) outward by the threadable insertion of the jack screw 80 so that the flange projections 66 are deployed into the pedicle cut 92.

Figure 28:
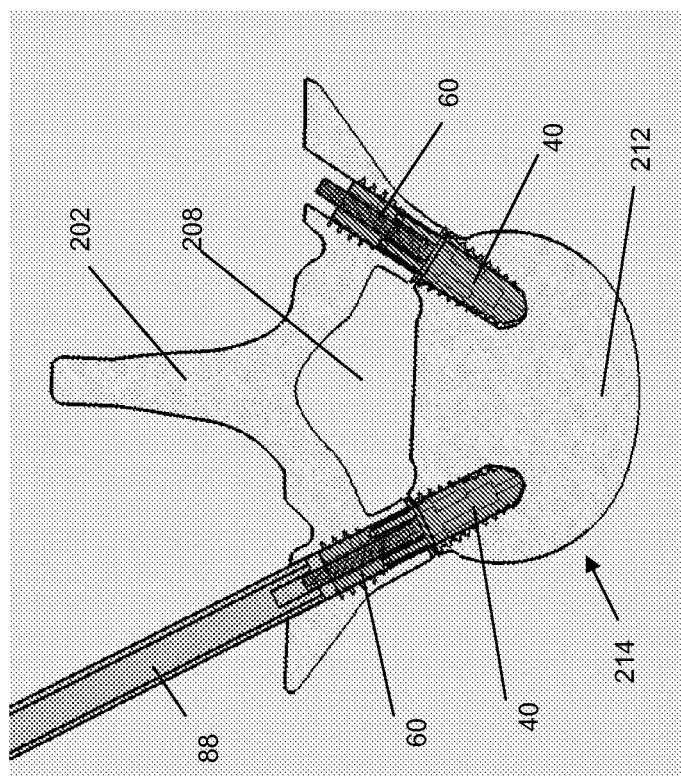
FIG. 28 illustrates a cross-sectional view of a vertebrae following placement of the upper and lower implant portions, and with deployment of expandable flanges from the upper portion of the implant, in accordance with one preferred embodiment of the invention.

FIG. 28 illustrates a vertebra 214 after the sequence of pedicle preparation and implant insertion as shown in FIGS. 17-25 have been repeated on the opposite pedicle 206 of the vertebra 214.

Figure 29:
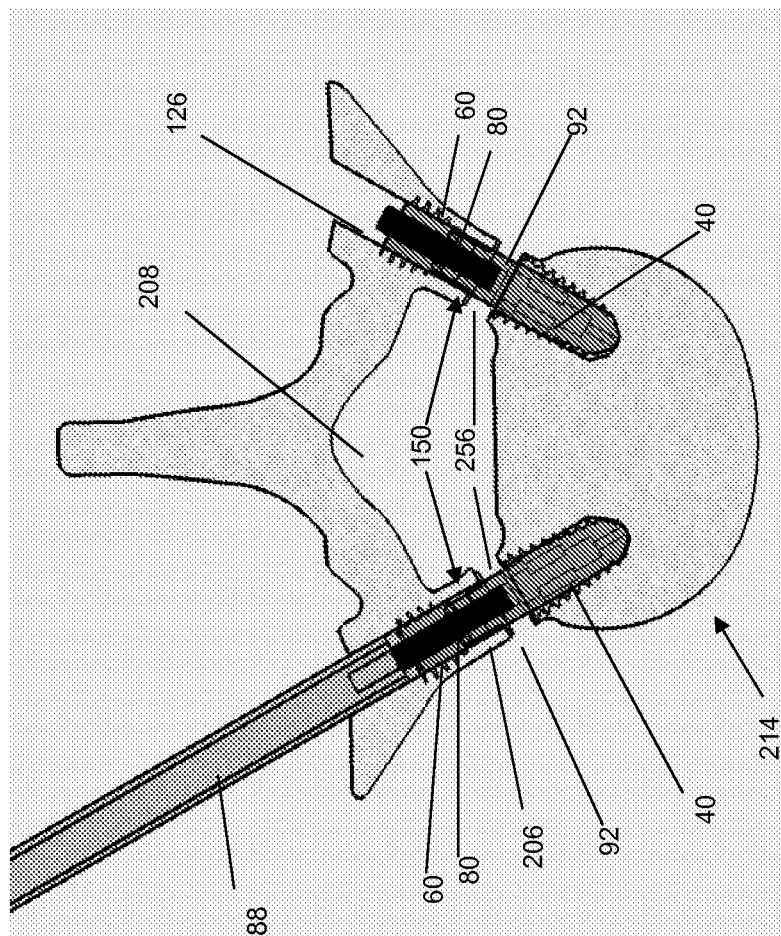
FIG. 29 illustrates a cross-sectional view of a vertebrae following linear expansion of a gap between the cut edges of the pedicle, on both sides of the vertebrae.

FIG. 29 illustrates a vertebra 214 after lengthening of the pedicles 206 bilaterally. Note that further insertion of the jack screws 80 has caused further widening of the pedicle cut 92, thereby forming a gap 256. The pedicle lengthening devices 150 are in place within each pedicle 206, maintaining the lengthened state of the pedicles 206. Notice that the lengthening of the pedicles 206 has resulted in enlargement of the spinal canal 208.

FIGS. 30A-30C illustrate a locking bolt 120 threadably inserted into each upper 60 and each lower 40 implant portion to secure the pedicle lengthening devices 150 securely together and preserve the spinal canal 208 in the expanded state.

Figure 31:
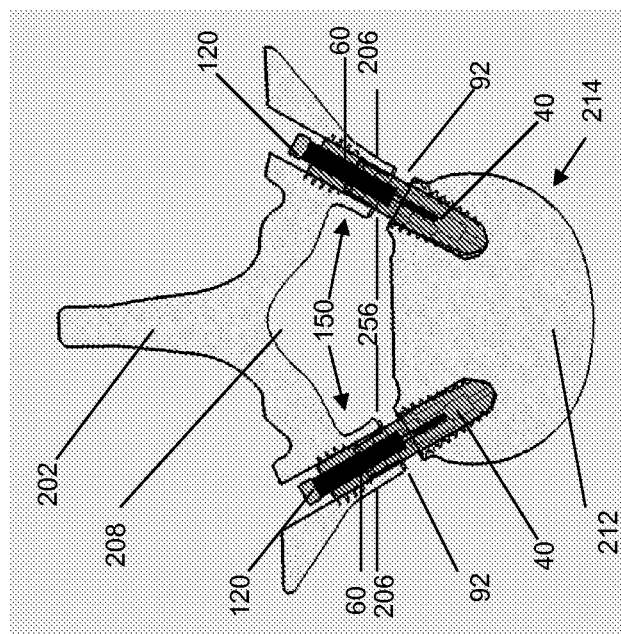
FIG. 31 illustrates a cross-sectional view of a vertebrae in a final lengthened state, with all components of one embodiment of the pedicle lengthening implant inserted to secure the construct and spinal canal in the expanded state.

FIG. 31 illustrates a final appearance of a preferred embodiment of the pedicle lengthening procedure. Both pedicles 206 have been lengthened and secured by the pedicle lengthening devices 150. The spinal canal 208 has been enlarged. The upper 60 and the lower 40 implant portions are fastened together and held by the locking bolt 120 so that bone healing of the pedicle gap 256 can occur.

Summary of Operation of Example Embodiments

A non-limiting summary of certain invention embodiments is provided as follows: First, a central pedicle bore 126 is drilled through a long axis of pedicles 206 using a drill 124 or related device (FIG. 19). The pedicle bore 126 is then created in such a way as to leave intact outer walls 129 of the pedicle 206 intact (FIG. 19). The drilling of the pedicle bore may be performed over a guide wire. The guide wire could be placed or the drilling could be performed using the guidance of x-ray, fluoroscopy, CAT scan or by image guided means, all techniques well known in the art of spinal surgery.

Figure 21:
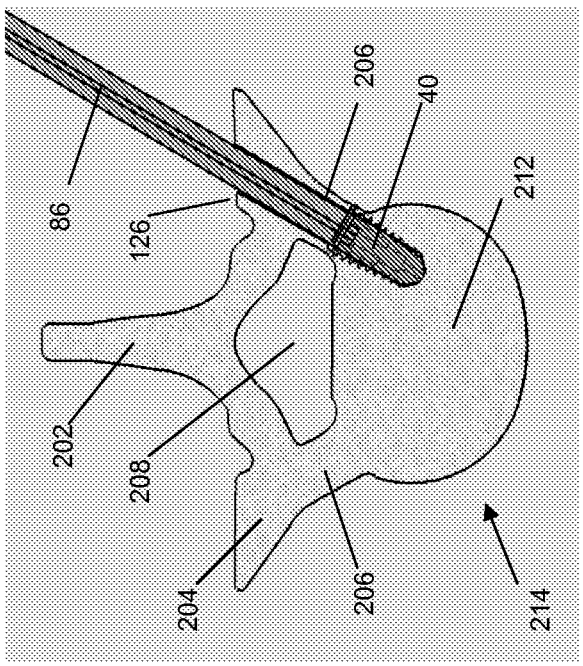
FIGS. 21A and 21B illustrate a cross-sectional view of a vertebrae undergoing the final seating of the lower implant into the pedicle bore using an insertion tool.
Figure 21:
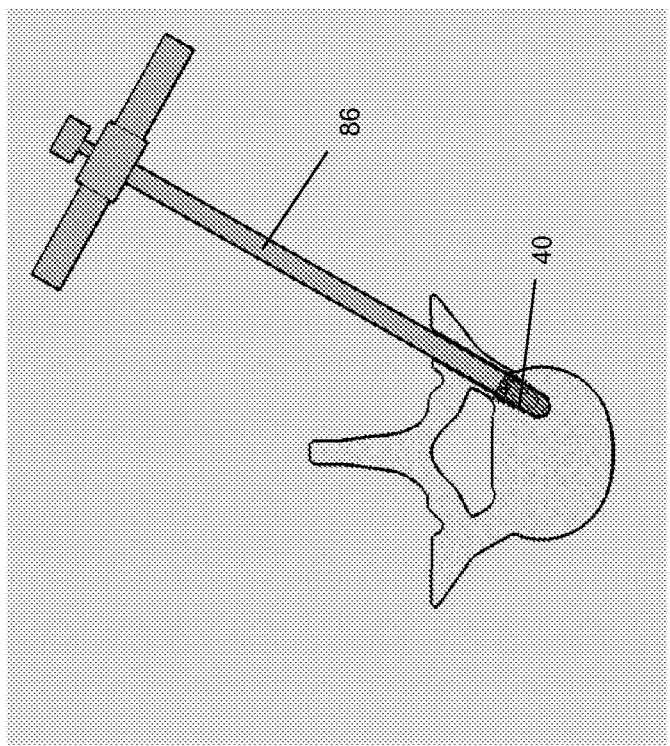
Figure 23:
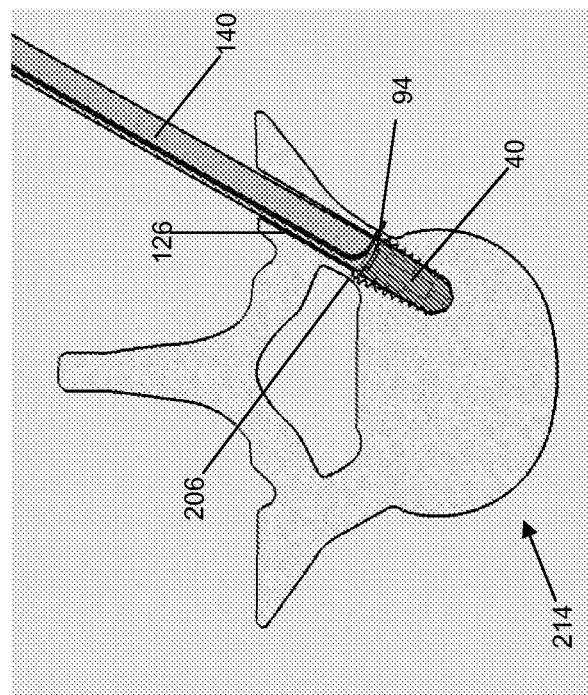
FIGS. 23A and 23B illustrate a cross-sectional view of a vertebrae undergoing cutting of a lateral portion of the pedicle wall using a linear pedicle saw, in accordance with one preferred embodiment of the invention.
Figure 23:
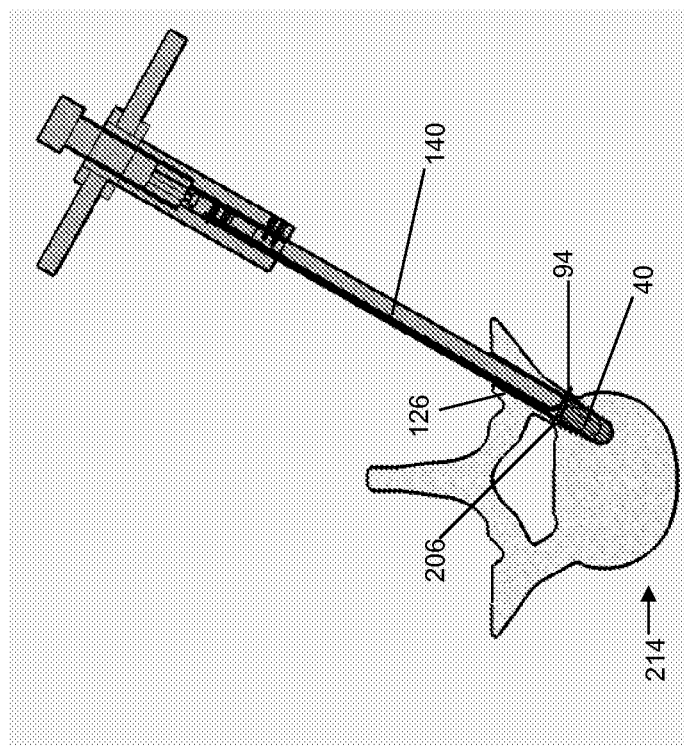

Next, a lower or distal implant portion 40 is placed into the pedicle bore 126 to a depth whereby the upper or proximal surface of the lower implant portion 40 is substantially localized at a junction between the pedicle 206 and a vertebral body 212 (FIGS. 20-22). Next, one or more bone saws 130, 140 are used to circumferentially cut or divide the pedicle 206 such that the pedicle wall 129 is completely sectioned with a circumferential bone cut 92 (FIGS. 23-24).

The radial bone saw 130, as illustrated in FIG. 15, works by placing the shaft of the saw 113 into the pedicle bore 126 (FIG. 22) until the trunnion 128 engages the lower implant portion 40. The radial saw blade 96 is deployed by turning the offset knob 118. The bone of the pedicle wall 129 is cut by rotating the saw handle 132 with sequentially increasing saw blade 96 deployment until an adequate depth of cut is achieved.

The linear saw 140, as shown is FIG. 13, works by placing the shaft of the saw 107 into the pedicle bore 126 (FIG. 22) until the trunnion 128 engages the lower implant portion 40. The flexible saw blade 94 is then deployed by turning the knob 127, causing the blade 94 to project from the side of the shaft 107. The linear saw 140 is turned in either a circumferential or "back-and-forth" motion to cut the bone of the pedicle wall 129 while sequentially increasing the length of flexible blade 94 deployment until the pedicle cut 92 (FIG. 24) is completed.

After the pedicle has been cut, the upper implant portion 60 is threadably inserted into the pedicle bore 126 until the upper implant 60 comes into contact with the lower implant portion 40 (FIGS. 25-26). Next, expanding flanges 90, 100 (FIG. 11) are deployed so that the flange projections 66 engage the pedicle cut 92 (FIG. 27). The deployment of the expandable flanges 90, 100 is achieved by the threadable advancement of the jack screw 80 (FIG. 27). Next, similar steps are repeated for the opposite pedicle (FIG. 28).

To achieve pedicle lengthening, the pedicle cuts 92 on both sides are then expanded to create gaps 256 by the further threadable advancement of the jack screw 80 on both sides of the vertebrae 214 (FIG. 29). By creating a gap 256 in the pedicles 206, the spinal canal 208 is enlarged (FIG. 29).

After the pedicles 206 have been lengthened, a locking bolt 120 is threadably inserted through the central regions of the pedicle lengthening device so that the upper 60 and the lower 40 portions of the pedicle lengthening device are securely locked together, thus securing the spinal canal 208 in the expanded state (FIGS. 30 and 31). With the pedicles 206 locked in the lengthened state, the pedicle gap 256 will heal, thus reconstituting the vertebrae 214 so that the spinal canal 208 would remain in a permanently enlarged state (FIG. 31).

To assist the vertebral healing process, portions of the pedicle lengthening device (such as the expandable flanges 90, 100) could be packed with an osteoconductive, osteoinductive or osteogenic material, to deliver the material to the pedicle bone cut 92 to promote the healing of bone across the site of the pedicle gap 256.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention.

What is claimed is:
1. A bone saw, comprising:
   a flexible saw blade, rectangular in shape over at least a portion of a length thereof, having a central longitudinal axis and a cutting edge at a distal tip;
   a shaft having:
      a central longitudinal axis;
      a blade passage within the shaft, the blade passage housing the saw blade, wherein the central longitudinal axis of the saw blade within the blade passage is separate from and parallel to the central longitudinal axis of the shaft;
      a blade opening located at and through a side of a distal end portion of the shaft;
      a curved abutment within the shaft, aligning the blade passage with the blade opening by concave curvature, wherein distally translating the saw blade within the blade passage causes the saw blade to concavely conform to the curved abutment and exit the blade opening;
   wherein the length of the saw blade is such that at least a portion thereof remains within the blade passage whether the saw blade is fully retracted within the shaft or fully advanced out of the blade opening.

2. The bone saw of claim 1, further comprising a trunnion at a distal tip of the shaft, the trunnion located distal of the blade opening, the trunnion facilitating placement of the distal tip of the shaft to precisely locate a desired blade opening location.

3. The bone saw of claim 1, further comprising a threaded drive mechanism located at a proximal end of the shaft and communicating with the saw blade, wherein distally advancing the threaded drive mechanism distally translates the saw blade within the blade passage, causing the cutting edge to exit the blade opening, and proximally retracting the threaded drive mechanism proximally translates the saw blade within the blade passage, causing the cutting edge to retract into the blade opening.

4. The bone saw of claim 3, further comprising a depth indicator located at a proximal end of the shaft and communicating with the threaded drive mechanism, wherein a distance of advancing or retracting the drive mechanism, associated with a length of advancing of the cutting edge out of the blade opening, is indicated on the depth indicator.

5. The bone saw of claim 4, wherein the depth indicator extends proximally from the threaded drive mechanism and longitudinally relative to the shaft, where a distance of proximal extension of the depth indicator from the threaded drive mechanism is associated with a distance the cutting edge of the saw blade protrudes from the blade opening.

6. The bone saw of claim 1, wherein the blade opening includes an indentor extending therein, the indentor being a raised portion centrally located on a distal edge of the blade opening, whereby the indentor is configured to introduce a crimp or counter bend to the saw blade when the saw blade passes there over while exiting the blade opening.

7. The bone saw of claim 1, wherein the blade opening includes an indentor extending therein, the indentor being a raised portion centrally located on a distal edge of the blade opening, whereby the indentor is configured to align with a groove in the saw blade as the saw blade exits the blade opening, thereby facilitating blade positioning and cutting control.

8. A bone saw, comprising:
- a flexible saw blade, rectangular in shape over at least a portion of a length thereof, having a cutting edge at a distal tip;
- a shaft having:
  - a central longitudinal axis;
  - a blade passage within the shaft, the blade passage housing the saw blade;
  - a blade opening located at and through a side of a distal end portion of the shaft; and
  - an abutment within the shaft, aligning the blade passage with the blade opening, wherein distally translating the saw blade within the blade passage causes the saw blade to conform to the abutment and exit the blade opening;
- wherein:
  - the saw blade further comprises a longitudinal groove along a side thereof; and
  - the blade opening further comprises an indentor penetrating therein, the indentor positioned to align with the groove of the saw blade as the saw blade exits the blade opening, thereby facilitating desired blade alignment upon exiting the blade opening.

9. A bone saw, comprising:
- a flexible saw blade, rectangular in shape over at least a portion of a length thereof, having a cutting edge at a distal tip;
- a shaft having:
  - a central longitudinal axis;
  - a blade passage within the shaft, the blade passage housing the saw blade;
  - a blade opening located at and through a side of a distal end portion of the shaft; and
  - an abutment within the shaft, aligning the blade passage with the blade opening, wherein distally translating the saw blade within the blade passage causes the saw blade to conform to the abutment and exit the blade opening; and
- an indentor penetrating into the blade opening, the indentor configured to introduce a crimp or counter bend to the flexible saw blade, thereby counteracting a curling of the saw blade during a passing of the saw blade over the abutment within the shaft.

10. A bone saw, comprising:
- a flexible saw blade, rectangular in shape over at least a portion of a length thereof, having a central longitudinal axis and a cutting edge at a distal tip;
- a shaft having:
  - a central longitudinal axis;
  - a blade passage within the shaft, the blade passage housing the saw blade, wherein the central longitudinal axis of the saw blade within the blade passage is separate from and parallel to the central longitudinal axis of the shaft;
  - a blade opening located at and through a side of a distal end portion of the shaft;
  - an abutment within the shaft, aligning the blade passage with the blade opening, wherein distally translating the saw blade within the blade passage causes the saw blade to conform to the abutment and exit the blade opening;
- wherein the length of the saw blade is such that, whether the saw blade is fully retracted within the shaft or fully advanced out of the blade opening, the saw blade:
  - extends within the blade passage over a majority of the length of the shaft; and
  - at least a portion of the length of the saw blade remains within the blade passage and the central longitudinal axis of the saw blade within the blade passage is separate from and parallel to the central longitudinal axis of the shaft.

11. The bone saw of claim 10, wherein the abutment has concave curvature, the concave curvature aligning the blade passage with the blade opening, and where distally translating the saw blade within the blade passage causes the saw blade to concavely conform to the abutment and exit the blade opening.

12. The bone saw of claim 10, wherein the blade opening includes an indentor extending therein, the indentor being a raised portion centrally located on a distal edge of the blade opening, whereby the indentor is configured to introduce a crimp or counter bend to the saw blade when the saw blade passes there over while exiting the blade opening.

13. The bone saw of claim 10, wherein the blade opening includes an indentor extending therein, the indentor being a raised portion centrally located on a distal edge of the blade opening, whereby the indentor is configured to align with a groove in the saw blade as the saw blade exits the blade opening, thereby facilitating blade positioning and cutting control.

14. The bone saw of claim 10, further comprising a trunnion at a distal tip of the shaft, the trunnion located distal of the blade opening, the trunnion facilitating placement of the distal tip of the shaft to precisely locate a desired blade opening location.

15. The bone saw of claim 10, further comprising a threaded drive mechanism located at a proximal end of the shaft and communicating with the saw blade, wherein distally advancing the threaded drive mechanism distally translates the saw blade within the blade passage, causing the cutting edge to exit the blade opening, and proximally retracting the threaded drive mechanism proximally translates the saw blade within the blade passage, causing the cutting edge to retract into the blade opening.

16. The bone saw of claim 15, further comprising a depth indicator located at a proximal end of the shaft and communicating with the threaded drive mechanism, wherein a distance of advancing or retracting the drive mechanism, associated with a length of advancing of the cutting edge out of the blade opening, is indicated on the depth indicator.

17. The bone saw of claim 16, wherein the depth indicator extends proximally from the threaded drive mechanism and longitudinally relative to the shaft, where a distance of proximal extension of the depth indicator from the threaded drive mechanism is associated with a distance the cutting edge of the saw blade protrudes from the blade opening.

18. The bone saw of claim 10, further comprising:
- a drive mechanism located at a proximal end portion of the shaft and communicating with the saw blade, wherein distally advancing the drive mechanism distally translates the saw blade within the blade passage, causing the cutting edge of the saw blade to exit the blade opening; and
- a depth indicator that displays a length of advancement of the cutting edge of the saw blade out of the blade opening, the depth indicator extending proximally from the drive mechanism and longitudinally relative to the shaft, where a distance of proximal extension of the depth indicator from the drive mechanism is associated with the advancement of the cutting edge of the saw blade out of the blade opening.

* * * * *